US012788458B2

(12) United States Patent
Skinlo et al.

(10) Patent No.: US 12,788,458 B2
(45) Date of Patent: Nov. 10, 2026

(54) ADJUSTABLE DEVICES FOR TREATING ARTHRITIS OF THE KNEE

(71) Applicant: NuVasive Specialized Orthopedics, Inc., San Diego, CA (US)

(72) Inventors: David Skinlo, North Logan, UT (US); Thomas B. Buford, Laguna Beach, CA (US); Ephraim Akyuz, Logan, UT (US); Thomas Weisel, Ventura, CA (US); Roger Pisarnwongs, Valencia, CA (US); Adam G. Beckett, Mission Viejo, CA (US); Jeffrey Lee Gilbert, Lake Forest, CA (US); Frank Yan Liu, Irvine, CA (US); Urs Weber, Irvine, CA (US); Edmund J. Roschak, Mission Viejo, CA (US); Blair Walker, Mission Viejo, CA (US); Scott Pool, Laguna Hills, CA (US); Mark T. Dahl, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 19/206,518

(22) Filed: May 13, 2025

(65) Prior Publication Data

US 2025/0268635 A1 Aug. 28, 2025

Related U.S. Application Data

(63) Continuation of application No. 18/410,052, filed on Jan. 11, 2024, now Pat. No. 12,295,630, which is a (Continued)

(51) Int. Cl.

*A61B 17/02* (2006.01)
*A61B 6/12* (2006.01)

(Continued)

(52) U.S. Cl.

CPC ............ *A61B 17/8095* (2013.01); *A61B 6/12* (2013.01); *A61B 17/1675* (2013.01); *A61B 17/7216* (2013.01); *A61B 17/8004* (2013.01); *A61B 17/8023* (2013.01); *A61B 17/8061* (2013.01); *A61B 17/8852* (2013.01); *A61B 17/8872* (2013.01); *A61B 2017/00212* (2013.01);

(Continued)

(58) Field of Classification Search

CPC ............ A61B 17/1675; A61B 17/1677; A61B 17/1682; A61B 17/1684; A61B 17/1686; A61B 17/025; A61B 2017/0268; A61B 2017/0275; A61B 2017/0256

See application file for complete search history.

(56) References Cited

U.S. PATENT DOCUMENTS

2011/0060336 A1* 3/2011 Pool .................. A61B 17/1725 606/62

* cited by examiner

*Primary Examiner* — Samuel S Hanna

(57) ABSTRACT

A system for surgical planning and assessment of spinal deformity correction is provided that has a spinal imaging system and a control unit. The spinal imaging system is configured to collect at least one digitized position of one or more vertebral bodies of a subject. The control unit is configured to receive the at least one digitized position, and calculate, based on the at least one digitized position, an optimized posture for the subject. The control unit is configured to receive one or more simulated spinal correction inputs, and based on the inputs and optimized posture, predict an optimal simulated postoperative surgical correction.

8 Claims, 38 Drawing Sheets

Related U.S. Application Data continuation of application No. 17/544,856, filed on Dec. 7, 2021, now Pat. No. 11,871,971, which is a continuation of application No. 16/159,061, filed on Oct. 12, 2018, now Pat. No. 11,213,330, which is a continuation of application No. 14/379,742, filed as application No. PCT/US2013/067142 on Oct. 28, 2013, now Pat. No. 10,130,405.

(60) Provisional application No. 61/868,535, filed on Aug. 21, 2013, provisional application No. 61/719,887, filed on Oct. 29, 2012.

(51) Int. Cl.

| | |
|---|---|
| ***A61B 17/16*** | (2006.01) |
| ***A61B 17/72*** | (2006.01) |
| ***A61B 17/80*** | (2006.01) |
| ***A61B 17/88*** | (2006.01) |
| *A61B 17/00* | (2006.01) |
| *A61B 17/56* | (2006.01) |
| *A61B 17/68* | (2006.01) |
| *A61B 17/70* | (2006.01) |
| *A61F 2/38* | (2006.01) |

(52) U.S. Cl.

CPC ............... *A61B 2017/00402* (2013.01); *A61B 2017/00411* (2013.01); *A61B 2017/00539* (2013.01); *A61B 2017/00544* (2013.01); *A61B 2017/00734* (2013.01); *A61B 2017/00867* (2013.01); *A61B 2017/00876* (2013.01); *A61B 2017/00991* (2013.01); *A61B 2017/564* (2013.01); *A61B 2017/681* (2013.01); *A61B 17/7016* (2013.01); *A61B 17/7017* (2013.01); *A61F 2/389* (2013.01)

ADJUSTABLE DEVICES FOR TREATING ARTHRITIS OF THE KNEE

CROSS REFERENCE TO RELATED APPLICATIONS

This application is a continuation of U.S. patent application Ser. No. 18/410,052, filed Jan. 11, 2024, which is a continuation of U.S. patent application Ser. No. 17/544,856, which is a continuation of U.S. patent application Ser. No. 16/159,061, filed Oct. 12, 2018 (now U.S. Pat. No. 11,213,330), which is a continuation of U.S. patent application Ser. No. 14/379,742, filed Aug. 19, 2014 (now U.S. Pat. No. 10,130,405), which is a National Stage Entry of International Application No. PCT/US2013/067142, filed Oct. 28, 2013, which claims priority to U.S. Provisional Application No. 61/868,535, filed Aug. 21, 2013, and to U.S. Provisional Application No. 61/719,887, filed Oct. 29, 2012. The contents of each of the foregoing is incorporated by reference in its entirety as though fully set forth herein

BACKGROUND OF THE INVENTION

Field of the Invention

The field of the invention generally relates to medical devices for treating knee osteoarthritis.

Description of the Related Art

Knee osteoarthritis is a degenerative disease of the knee joint that affects a large number of patients, particularly over the age of 40. The prevalence of this disease has increased significantly over the last several decades, attributed partially, but not completely, to the rising age of the population as well as the increase in obesity. The increase may also be due to the increase in highly active people within the population. Knee osteoarthritis is caused mainly by long term stresses on the knee that degrade the cartilage covering the articulating surfaces of the bones in the knee joint. Oftentimes, the problem becomes worse after a particular trauma event, but it can also be a hereditary process. Symptoms include pain, stiffness, reduced range of motion, swelling, deformity, muscle weakness, and several others. Osteoarthritis may include one or more of the three compartments of the knee: the medial compartment of the tibiofemoral joint, the lateral compartment of the tibiofemoral joint, and the patellofemoral joint. In severe cases, partial or total replacement of the knee is performed in order to replace the diseased portions with new weight bearing surfaces for the knee, typically made from implant grade plastics or metals. These operations involve significant post-operative pain and require substantial physical therapy. The recovery period may last weeks or months. Several potential complications of this surgery exist, including deep venous thrombosis, loss of motion, infection and bone fracture. After recovery, surgical patients who have received uni-compartmental or total knee replacement must significantly reduce their activity, removing running and high energy sports completely from their lifestyle.

For these reasons, surgeons are attempting to intervene early in order to delay or even preclude knee replacement surgery. Osteotomy surgeries may be performed on the femur or tibia, in order to change the angle between the femur and tibia, and thus adjust the stresses on the different portions of the knee joint. In closed wedge or closing wedge osteotomy, an angled wedge of bone is removed, and the remaining surfaces are fused together, creating a new improved bone angle. In open wedge osteotomy, a cut is made in the bone and the edges of the cut are opened, creating a new angle. Bone graft is often used to fill in the new opened wedge-shaped space, and often, a plate is attached to the bone with bone screws. Obtaining the correct angle during either of these types of osteotomy is almost always suboptimal, and even if the result is close to what was desired, there can be a subsequent loss of the correction angle. Some other complications experienced with this technique include nonunion and material failure.

SUMMARY OF THE INVENTION

In a first embodiment of the invention, a system for changing an angle of a bone of a subject includes an adjustable actuator having an outer housing and an inner shaft, telescopically disposed in the outer housing, a magnetic assembly configured to adjust the length of the adjustable actuator though axial movement of the inner shaft and outer housing in relation to one another, a first bracket configured for coupling to the outer housing, and a second bracket configured for coupling to the inner shaft, wherein application of a moving magnetic field externally to the subject moves the magnetic assembly such that the inner shaft and the outer housing move in relation to one another.

In another embodiment of the invention, a system for changing an angle of a bone of a subject includes a magnetic assembly having a radially-poled magnet coupled to a shaft having external threads, and a block having internal threads and coupled to the shaft, wherein rotational movement of the radially-poled magnet causes the shaft to turn and to move axially in relation to the block. The system further includes an upper bone interface and a lower bone interface having an adjustable distance, wherein axial movement of the shaft in a first direction causes the distance to increase.

In another embodiment of the invention, a system for changing an angle of a bone of a subject includes a scissors assembly having first and second scissor arms pivotably coupled via a hinge, the first and second scissor arms coupled, respectively, to upper and lower bone interfaces configured to move relative to one another. The system further includes a hollow magnetic assembly containing an axially moveable lead screw disposed therein, wherein the hollow magnetic assembly is configured to rotate in response to a moving magnetic field and wherein said rotation translations into axial movement of the lead screw. The system further includes a ratchet assembly coupled at one end to the lead screw and at another end to one of the first and second scissor arms, the ratchet assembly comprising a pawl configured to engage teeth disposed in one of the upper and lower bone interfaces, and wherein axial movement of the lead screw advances the pawl along the teeth and moves the upper and lower bone interfaces away from one another.

In another embodiment of the invention, a method of preparing a tibia for implantation of an offset implant includes making a first incision in the skin of a patient at a location adjacent the tibial plateau of the tibia of the patient, creating a first cavity in the tibia by removing bone material along a first axis extending in a substantially longitudinal direction from a first point at the tibial plateau to a second point, placing an excavation device within the first cavity, the excavation device including a main elongate body and configured to excavate the tibia asymmetrically in relation to the first axis, creating a second cavity in the tibia with the excavation device, wherein the second cavity communicates with the first cavity and extends substantially towards one side of the tibia, and removing the excavation device.

In another embodiment of the invention, a method of implanting a non-invasively adjustable system for changing an angle of the tibia of a patient includes creating an osteotomy between a first portion and a second portion of the tibia, making a first incision in the skin of a patient at a location adjacent the tibial plateau of the tibia of the patient, creating a first cavity in the tibia along a first axis extending in a substantially longitudinal direction from a first point at the tibial plateau to a second point, placing an excavation device within the first cavity, the excavation device configured to excavate the tibia asymmetrically in relation to the first axis, creating a second cavity in the tibia with the excavation device, wherein the second cavity extends substantially towards one side of the tibia, placing a non-invasively adjustable implant through the first cavity and at least partially into the second cavity, the non-invasively adjustable implant comprising an adjustable actuator having an outer housing and an inner shaft, telescopically disposed in the outer housing, coupling the outer housing to the first portion of the tibia, and coupling the inner shaft to the second portion of the tibia. In some embodiments, the implant could also be adjusted invasively, such as minimally invasively.

In another embodiment of the invention, a method of preparing a bone for implantation of an implant includes making a first incision in the skin of a patient, creating a first cavity in the bone by removing bone material along a first axis extending in a substantially longitudinal direction from a first point at the tibial plateau to a second point, placing an excavation device within the first cavity, the excavation device including a main elongate body and configured to excavate the bone asymmetrically in relation to the first axis, the excavation device further comprising an articulating arm having a first end and a second end, the arm including a compaction surface, creating a second cavity in the bone with the excavation device, wherein the second cavity communicates with the first cavity and extends substantially towards one side of the bone, and removing the excavation device.

In another embodiment of the invention, a method of preparing a bone for implantation of an implant includes making a first incision in the skin of a patient, creating a first cavity in the bone by removing bone material along a first axis extending in a substantially longitudinal direction from a first point at the tibial plateau to a second point, placing an excavation device within the first cavity, the excavation device including a main elongate body and configured to excavate the bone asymmetrically in relation to the first axis, the excavation device further comprising an articulating arm having a first end and a second end, the arm including an abrading surface, creating a second cavity in the bone with the excavation device, wherein the second cavity communicates with the first cavity and extends substantially towards one side of the bone, and removing the excavation device.

In another embodiment of the invention, a method of preparing a bone for implantation of an implant includes making a first incision in the skin of a patient, creating a first cavity in the bone by removing bone material along a first axis extending in a substantially longitudinal direction from a first point at the tibial plateau to a second point, placing an excavation device within the first cavity, the excavation device including a main elongate body and configured to excavate the bone asymmetrically in relation to the first axis, the excavation device further comprising a rotational cutting tool configured to be moved substantially towards one side of the bone while the rotational cutting tool is being rotated, creating a second cavity in the bone with the excavation device, wherein the second cavity communicates with the first cavity and extends substantially towards one side of the bone, and removing the excavation device.

In another embodiment of the invention, a system for changing an angle of a bone of a subject includes a non-invasively adjustable implant comprising an adjustable actuator having an outer housing and an inner shaft, telescopically disposed in the outer housing, the outer housing configured to couple to a first portion of the bone, and the inner shaft configured to couple to a second portion of the bone, a driving element configured to move the inner shaft in relation to the outer housing, and an excavation device including a main elongate body configured to insert within a first cavity of the bone along a first axis, the excavation device configured to excavate the bone asymmetrically in relation to the first axis to create a second cavity communicating with the first cavity, wherein the adjustable actuator is configured to be coupled to the bone at least partially within the second cavity.

In another embodiment of the invention, a method of changing a bone angle includes creating an osteotomy between a first portion and a second portion of a tibia of a patient; creating a cavity in the tibia by removing bone material along an axis extending in a substantially longitudinal direction from a first point at the tibial plateau to a second point; placing a non-invasively adjustable implant into the cavity, the non-invasively adjustable implant comprising an adjustable actuator having an outer housing and an inner shaft, telescopically disposed in the outer housing, and a driving element configured to be remotely operable to telescopically displace the inner shaft in relation to the outer housing; coupling one of the outer housing or the inner shaft to the first portion of the tibia; coupling the other of the outer housing or the inner shaft to the second portion of the tibia; and remotely operating the driving element to telescopically displace the inner shaft in relation to the outer housing, thus changing an angle between the first portion and second portion of the tibia.

In another embodiment of the invention, a system for changing an angle of a tibia of a subject having osteoarthritis of the knee includes a non-invasively adjustable implant comprising an adjustable actuator configured to be placed inside a longitudinal cavity within the tibia, and having an outer housing and an inner shaft, telescopically disposed in the outer housing, the outer housing configured to couple to a first portion of the tibia, and the inner shaft configured to couple to a second portion of the tibia, the second portion of the tibia separated at least partially from the first portion of the tibia by an osteotomy; and a driving element comprising a permanent magnet and configured to be remotely operable to telescopically displace the inner shaft in relation to the outer housing.

In another embodiment of the invention, a system for changing an angle of a bone of a subject includes a non-invasively adjustable implant comprising an adjustable actuator having an outer housing and an inner shaft, telescopically disposed in the outer housing, the outer housing associated with a first anchor hole, and the inner shaft associated with a second anchor hole, the first anchor hole configured to pass a first anchor for coupling the adjustable actuator to a first portion of the bone and the second anchor hole configured to pass a second anchor for coupling the adjustable actuator to a second portion of the bone, the second portion of the bone separated at least partially from the first portion of the bone by an osteotomy; a driving element configured to be remotely operable to telescopically displace the inner shaft in relation to the outer housing; and wherein the non-invasively adjustable implant is configured to be angularly unconstrained in relation to at least one of the first portion of the bone or the second portion of the bone when coupled to both the first portion and second portion of the bone.

DETAILED DESCRIPTION OF THE ILLUSTRATED EMBODIMENTS

Figure 1:
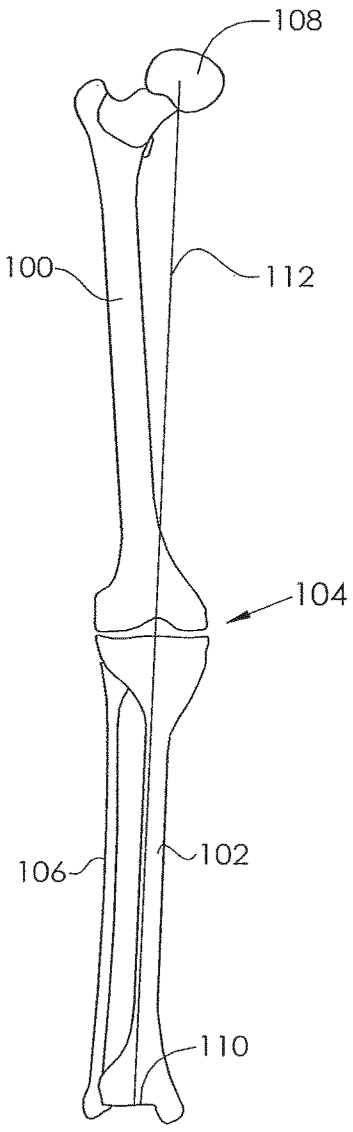
FIG. 1 illustrates the desired alignment of a knee joint in relation to a femur and tibia.
Figure 2:
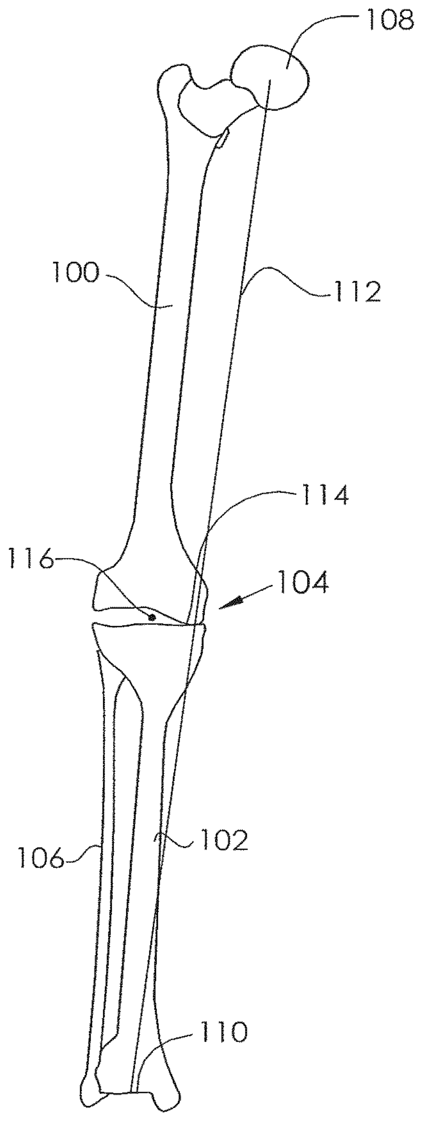
FIG. 2 illustrates a knee joint with misalignment and associated medial compartment osteoarthritis.

FIG. 1 illustrates a standard alignment of a femur 100, a tibia 102 and a knee joint 104, wherein a hip joint (at a femur head 108), a knee joint 104 and an ankle joint (at the midline of distal tibia 110) are oriented along a single line 112. A fibula 106 is shown alongside the tibia 102. The knee joint 104 of FIG. 2 is shown in an arthritic state, in which a medial compartment 114 has been compromised, causing the line 112 to pass medially off the center of the knee joint 104.

Figure 3:
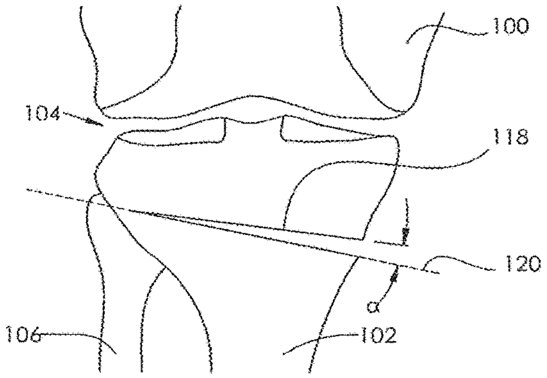
FIG. 3 PRIOR ART
FIG. 3 illustrates an open wedge technique in a tibia.
Figure 4:
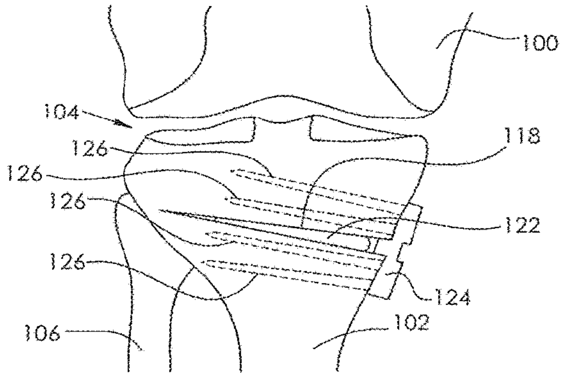
FIG. 4 PRIOR ART
FIG. 4 illustrates an open wedge technique with bone graft and a plate attached.

FIG. 3 illustrates an open wedge osteotomy 118 formed by making a cut along a cut line 120, and opening a wedge angle α. FIG. 4 illustrates the final setting of this open wedge by the placement of bone graft material 122 within the open wedge osteotomy 118, and then placement of a plate 124, which is then secured to the tibia 102 with tibial screws 126.

Figure 5:
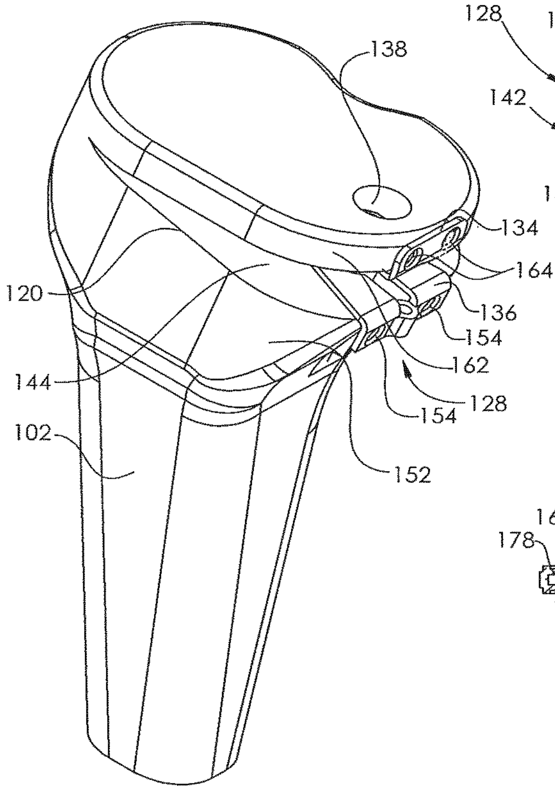
FIG. 5 illustrates a non-invasively adjustable wedge osteotomy device placed in a tibia according to a first embodiment of the present invention placed in a tibia.

FIG. 5 illustrates a tibia 102 with a non-invasively adjustable wedge osteotomy device 128 implanted. The non-invasively adjustable wedge osteotomy device 128 is shown without the tibia 102 in FIG. 6. The non-invasively adjustable wedge osteotomy device 128 includes an actuator 142 comprising an outer housing 130 and an inner shaft 132 telescopically coupled within the outer housing 130 for non-invasive longitudinal adjustment. To implant the non-invasively adjustable wedge osteotomy device 128, a hole 138 is drilled in the tibia 102, and then a cut is made along cut line 120. The actuator 142 is then inserted, distal end 140 first, into the hole 138. A wedge opening 144 is opened enough to be able to insert a lower bracket 136 and an upper bracket 134. The lower bracket 136, as seen in FIG. 7, has an opening 146 and an internal diameter 148 which allow it to be snapped onto a circumferential groove 150 around the outer housing 130. The lower bracket 136 is then secured to the tibia 102 at the lower portion 152 of the wedge opening 144 by placing bone screws (not shown) through screw holes 154. Upper bracket 134 is then slid into place and secured to a proximal end 156 of the actuator 142 by tightening a tightening screw 158 which threads through a threaded hole in inner shaft 132 of the actuator 142. The upper bracket 134 is then secured to the tibia 102 at the upper portion 162 of the wedge opening 144 by placing bone screws (not shown) through screw holes 164.

Figure 6:
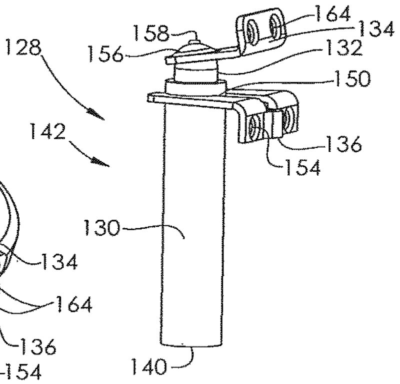
FIG. 6 illustrates a view of the non-invasively adjustable wedge osteotomy device of FIG. 5.
Figure 7:
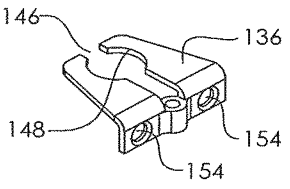
FIG. 7 illustrates a detailed view of the lower clip of the non-invasively adjustable wedge osteotomy device of FIGS. 5 and 6.
Figure 8:
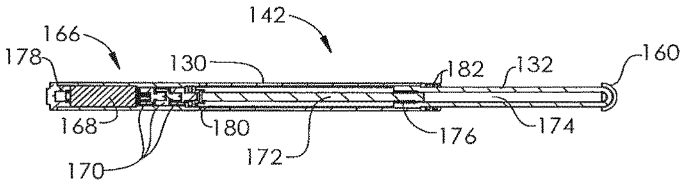
FIG. 8 illustrates an embodiment of a magnetically adjustable implant.

FIG. 8 illustrates a magnetically adjustable actuator 142 which can be used in the embodiments of FIGS. 5-7, or other embodiments described herein. An inner shaft 132, having an end 160, is telescopically adjustable within an outer housing 130 by the use of a magnetic assembly 166 contained therein. The magnetic assembly 166 comprises a radially-poled, cylindrical magnet 168 which engages with one or more planetary gear stages 170. The planetary gear stages 170 output to a lead screw 172. In some embodiments, the final gear stage 170 may be pinned to the lead screw 172 with a high strength pin, for example, a pin constructed from 400 series stainless steel. The inner shaft 132 contains a cavity 174 into which is bonded a nut 176 having a female thread which interfaces with the male thread of the lead screw 172. A radial bearing 178 and a thrust bearing 180 allow the magnetic assembly 166 to operate with relatively low friction. An o-ring seal 182 is held within a circumferential groove on inside of the wall of the outer housing 130, and the inner diameter of the o-ring seal 182 dynamically seals the outer diameter of the inner shaft 132.

Returning to FIG. 5, the non-invasively adjustable wedge osteotomy device 128 is used to gradually open the wedge opening 144 over time. By applying a moving magnetic field from an external location relative to the patient, for example, after the patient has recovered from surgery, the actuator 142 of FIG. 6 can be gradually lengthened (for example about one (1) mm per day), allowing the wedge opening 144 to reach a desired angle, which can be tested by having the patient perform different motion studies (stepping, turning, etc.), until the most comfortable condition is reached. Gradual lengthening can allow for the possibility of Ilizarov osteogenesis, in which new bone material forms in the wedge opening as it is opened. In such manner, a bone graft may be unnecessary. After the desired wedge opening 144 angle is reached, the newly grown bone material can be allowed to consolidate. If, during the process, lengthening has been too rapid, or new bone has not consolidated sufficiently, a moving magnetic field may be applied in an opposite direction thereby shortening the actuator 142 to add compression and create a good dimension for callus formation. After confirming that sufficient callus formation has taken place, lengthening may be resumed at the same speed, or at a different speed. Once lengthening is sufficiently completed, and consolidated bone is stable, it may be desired to remove the entire non-invasively adjustable wedge osteotomy device 128, or simply the magnetic assembly 166.

Figure 9:
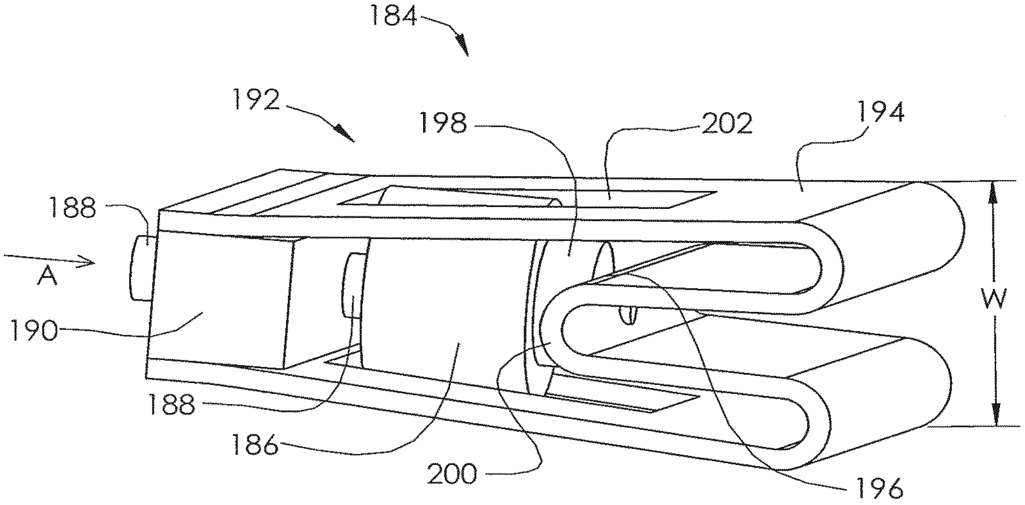
FIG. 9 illustrates a non-invasively adjustable wedge osteotomy device based on a spring element according to a second embodiment of the present invention.

FIG. 9 illustrates a non-invasively adjustable wedge osteotomy device 184 comprising magnetic assembly 192 including a magnet, e.g., a radially-poled cylindrical magnet 186 which is coupled to a drive screw 188. As radially-poled cylindrical magnet 186 is turned by an externally applied moving magnetic field, the drive screw 188 turns inside a block 190 having a female thread, causing the drive screw 188 and magnetic assembly 192 to be moved in a first axial direction (A). As the magnetic assembly 192 moves axially it pushes a curved shape memory (e.g., superelastic Nitinol®) plate spring 194 at connection point 196. A thrust bearing 198 at the connection point 196 allows for continued rotation of the radially-poled cylindrical magnet 186 as the force increases. As an inner curve 200 of the Nitinol plate spring 194 is pushed in the first axial direction (A), the width (W) of the Nitinol plate spring 194 increases. A cutout 202 in the Nitinol plate spring 194 provides space for the radially-poled cylindrical magnet 186 to turn and to move in the first axial direction (A).

Figure 10:
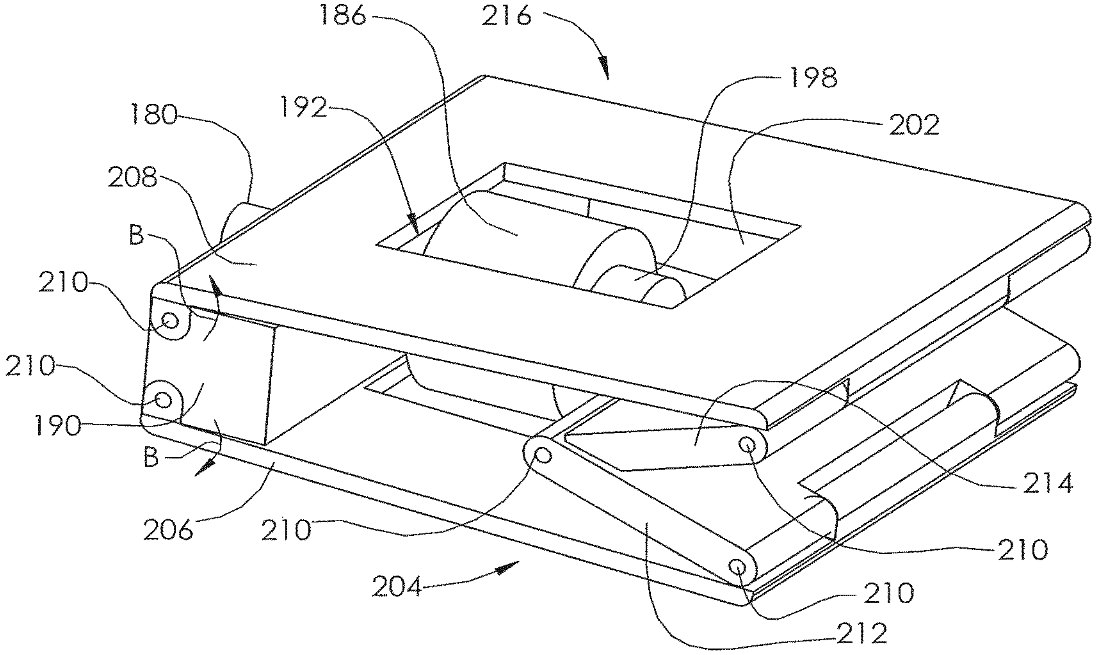
FIG. 10 illustrates a non-invasively adjustable wedge osteotomy device based on a linked lift according to a third embodiment of the present invention.

FIG. 10 illustrates a non-invasively adjustable wedge osteotomy device 216 similar to the non-invasively adjustable wedge osteotomy device 184 of FIG. 9, except that the Nitinol plate spring 194 of FIG. 9 is replaced by a linked lift 204. Linked lift 204 comprises a lower plate 206 and an upper plate 208 which are attached to a block 190 by pins 210 which allow each plate 206 and 208 to increase in angulation along arrows (B). Plates 206 and 208 are attached to inner plates 212 and 214 by pins 210. The hinged structure of inner plates 212, 214 is pushed forward in a similar manner as Nitinol plate spring 194 is pushed in the first axial direction (A) in FIG. 9.

Figure 11:
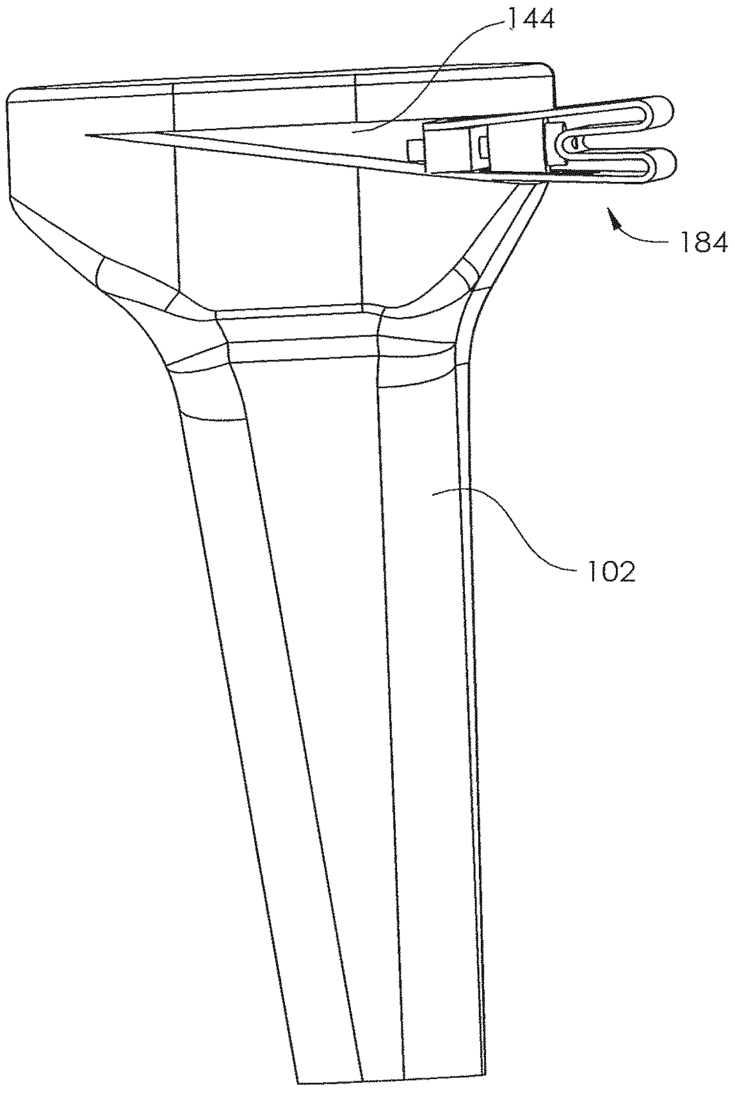
FIG. 11 illustrates the non-invasively adjustable wedge osteotomy device of FIG. 9 being inserted into a wedge opening in a tibia.

FIG. 11 illustrates the non-invasively adjustable wedge osteotomy device 184 being placed into a wedge opening 144 in a tibia 102. The non-invasively adjustable wedge osteotomy device 216 of FIG. 10 can be inserted in the same manner.

Figure 12:
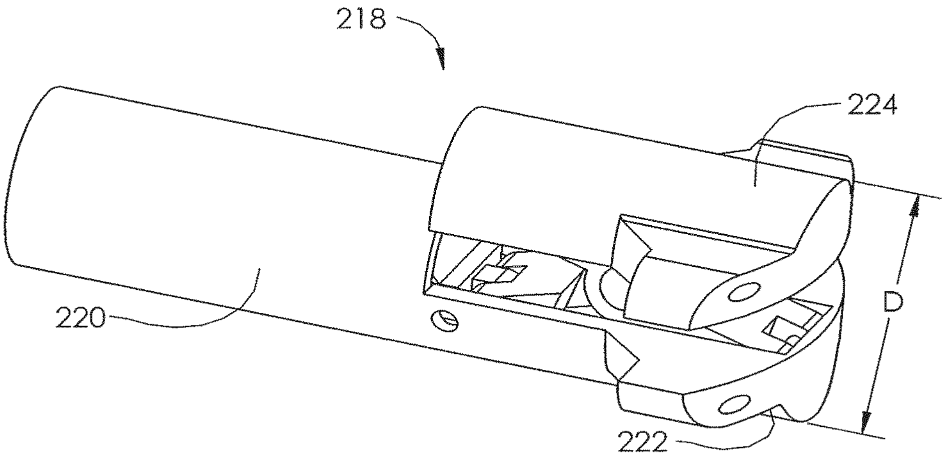
FIG. 12 illustrates a non-invasively adjustable wedge osteotomy device based on a scissor jack according to a fourth embodiment of the present invention.
Figure 13:
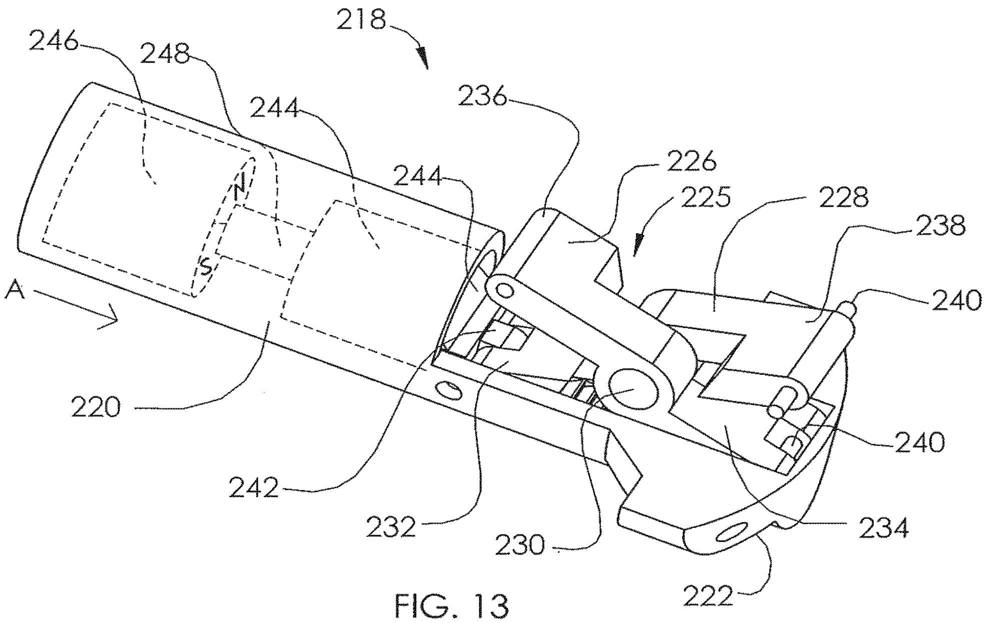
FIG. 13 illustrates the non-invasively adjustable wedge osteotomy device of FIG. 12 with the upper bone interface removed to show the scissor jack mechanism.
Figure 14:
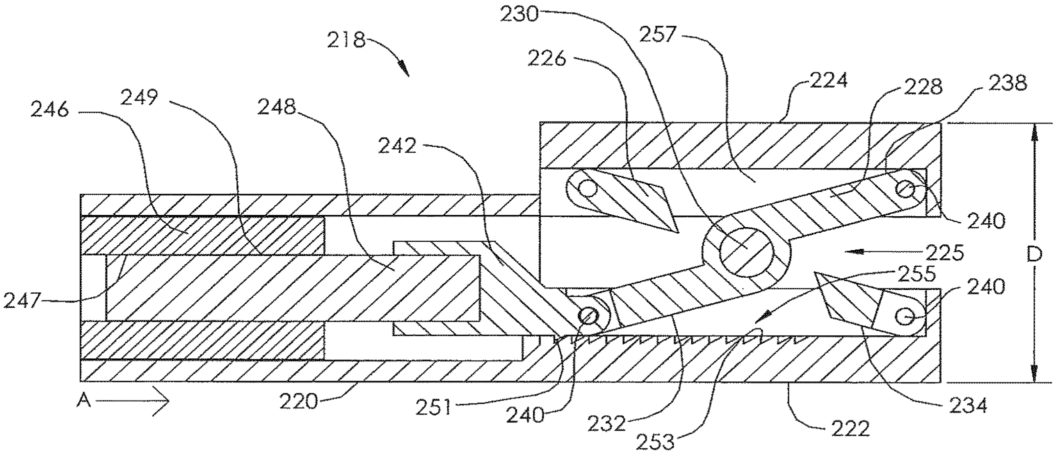
FIG. 14 illustrates a sectional view of the non-invasively adjustable wedge osteotomy device of FIGS. 12 and 13.

FIGS. 12-14 illustrate a non-invasively adjustable wedge osteotomy device 218 based on a scissor jack. Non-invasively adjustable wedge osteotomy device 218 comprises a main housing 220 having a lower bone interface 222 and an upper bone interface 224, the upper bone interface 224 which can be adjusted with respect to the main housing 220 and the lower bone interface 222. FIG. 13 shows the non-invasively adjustable wedge osteotomy device 218 with the upper bone interface 224 removed to better appreciate the inner components. A scissors assembly 225 comprises a first scissor 226 and a second scissor 228 that can be coupled by a center pin 230 in a hinged manner. Distal arms 234 and 238 of scissors 226 and 228 can be coupled to the distal ends of the lower bone interface 222 and the upper bone interface 224 by pins 240. An arm 232 of the second scissor 228 is coupled to an interconnect 242 of a magnetic assembly 244 with a pin 240. A hollow magnetic assembly 246 has internal threads 247 which engage external threads 249 of a lead screw 248 which is bonded to the interconnect 242. The hollow magnetic assembly 246 may comprise a hollow radially-poled magnet. The interconnect 242 includes a pawl 251, which is able to engage teeth 253 of a ratchet plate 255. As an externally applied moving magnetic field causes the magnet 246 to rotate, the lead screw 248 and the interconnect 242 are moved in a first axial direction (A), causing scissors assembly 225 to open up, and thus increase the distance (D) between the lower bone interface 222 and the upper bone interface 224. An arm 236 of the first scissor 226 is able to slide within a channel 257 in the upper bone interface 224. The pawl 251 and the teeth 253 of the ratchet plate 255 form a one way ratchet, allowing the distance (D) to be increased but not decreased.

Figure 15:
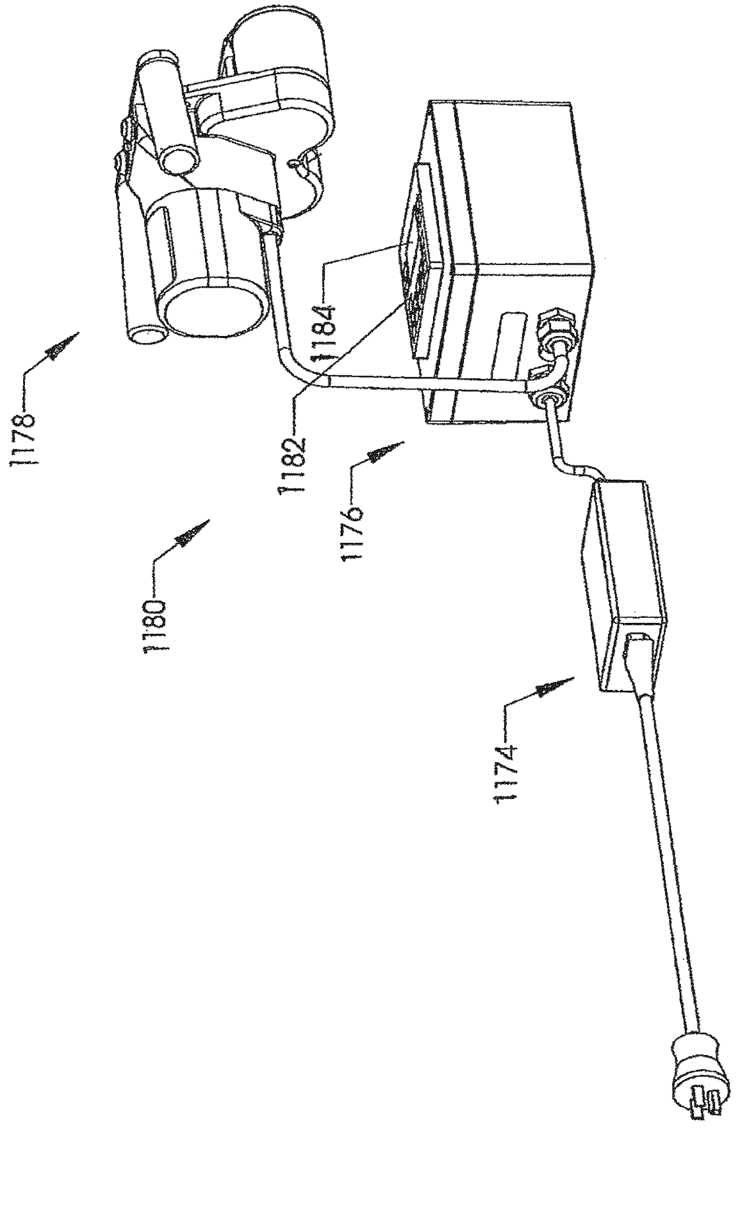
FIG. 15 illustrates a perspective view of an external adjustment device.

FIG. 15 illustrates an external adjustment device 1180 which is used to non-invasively adjust the devices and systems described herein. The external adjustment device 1180 comprises a magnetic handpiece 1178, a control box 1176 and a power supply 1174. The control box 1176 includes a control panel 1182 having one or more controls (buttons, switches or tactile, motion, audio or light sensors) and a display 1184. The display 1184 may be visual, auditory, tactile, the like or some combination of the aforementioned features. The external adjustment device 1180 may contain software which allows programming by the physician.

Figure 16:
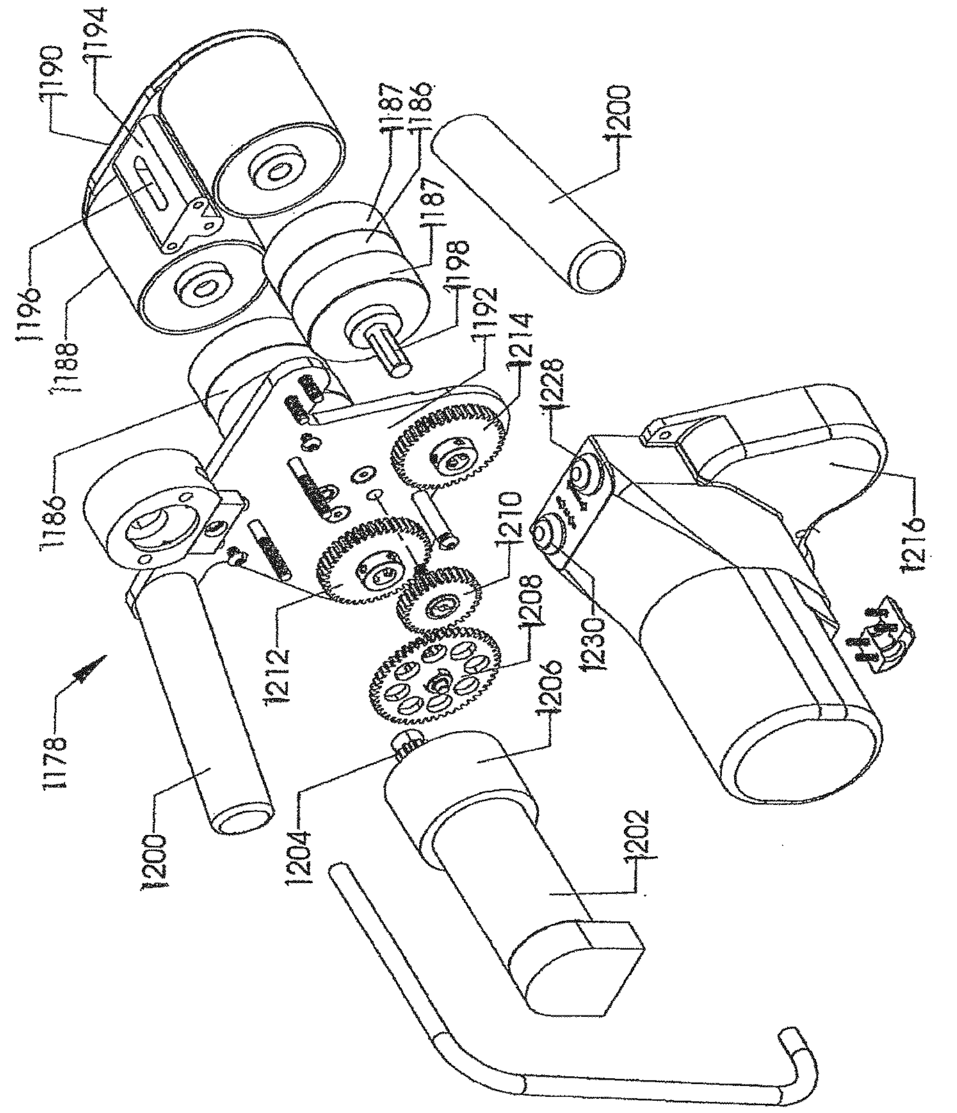
FIG. 16 illustrates an exploded view of a magnetic handpiece of the external adjustment device of FIG. 15.

FIG. 16 shows the detail of the magnetic handpiece 1178 of the external adjustment device 1180. As seen in FIG. 16, there are a plurality of, e.g., two (2), magnets 1186 that have a cylindrical shape (also, other shapes are possible). The magnets 1186 can be made from rare earth magnets, and can in some embodiments be radially poled. The magnets 1186 are bonded or otherwise secured within magnetic cups 1187. The magnetic cups 1187 include a shaft 1198 which is attached to a first magnet gear 1212 and a second magnet gear 1214, respectively. The orientation of the poles of each the two magnets 1186 are maintained in relation to each other by means of the gearing system (by use of center gear 1210, which meshes with both first magnet gear 1212 and second magnet gear 1214). In one embodiment, the north pole of one of the magnets 1186 turns synchronously with the south pole of the other magnet 1186, at matching clock positions throughout a complete rotation. The configuration has been known to provide an improved delivery of torque, for example to cylindrical magnet 168 or magnet 246. Examples of methods and embodiments of external adjustment devices that may be used to adjust the non-invasively adjustable wedge osteotomy device 218, or other embodiments of the present invention, are described in U.S. Pat. No. 8,382,756, the disclosure of which is hereby incorporated by reference in its entirety, and U.S. patent application Ser. No. 13/172,598 which was published with publication number 2012-0004494 A1, the disclosure of which is hereby incorporated by reference in its entirety.

The components of the magnetic handpiece 1178 are held together between a magnet plate 1190 and a front plate 1192. Most of the components are protected by a cover 1216. The magnets 1186 rotate within a static magnet cover 188, so that the magnetic handpiece 1178 may be rested directly on the patient, while not imparting any motion to the external surfaces of the patient. Prior to distracting the intramedullary lengthening device 1110, the operator places the magnetic handpiece 1178 over the patient near the location of the cylindrical magnet 1134. A magnet standoff 1194 that is interposed between the two magnets 1186 contains a viewing window 1196, to aid in the placement. For instance, a mark made on the patient's skin at the appropriate location with an indelible marker may be viewed through the viewing window 1196. To perform a distraction, the operator holds the magnetic handpiece 1178 by its handles 1200 and depresses a distract switch 1228, causing motor 1202 to drive in a first direction. The motor 1202 has a gear box 1206 which causes the rotational speed of an output gear 1204 to be different from the rotational speed of the motor 1202 (for example, a slower speed). The output gear 1204 then turns a reduction gear 1208 which meshes with center gear 1210, causing it to turn at a different rotational speed than the reduction gear 1208. The center gear 1210 meshes with both the first magnet gear 1212 and the second magnet gear 1214 turning them at a rate which is identical to each other. Depending on the portion of the body where the magnets 1186 of the external adjustment device 1180 are located, it is desired that this rate be controlled, to minimize the resulting induced current density imparted by magnet 1186 and cylindrical magnet 1134 though the tissues and fluids of the body. For example a magnet rotational speed of 60 RPM or less is contemplated although other speeds may be used such as 35 RPM or less. At any time, the distraction may be lessened by depressing the retract switch 1230, which can be desirable if the patient feels significant pain, or numbness in the area holding the device.

Figure 17:
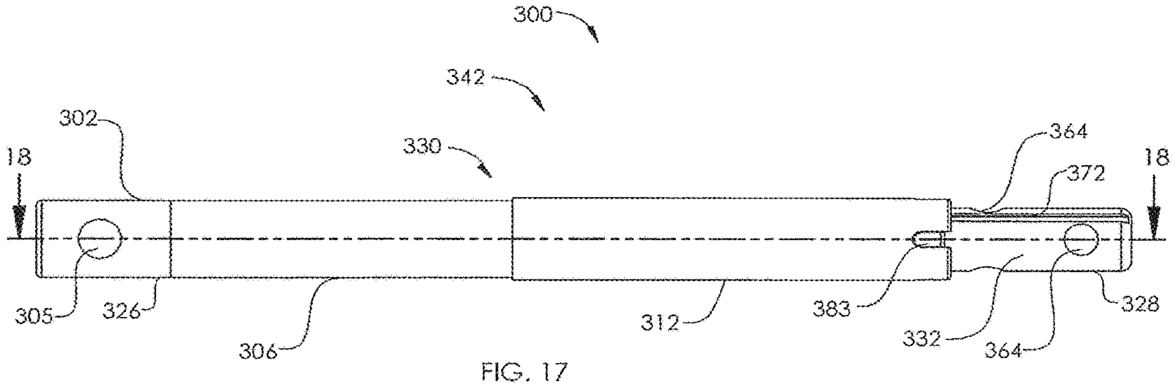
FIG. 17 illustrates a non-invasively adjustable wedge osteotomy device according to a fifth embodiment of the present invention.
Figure 18:
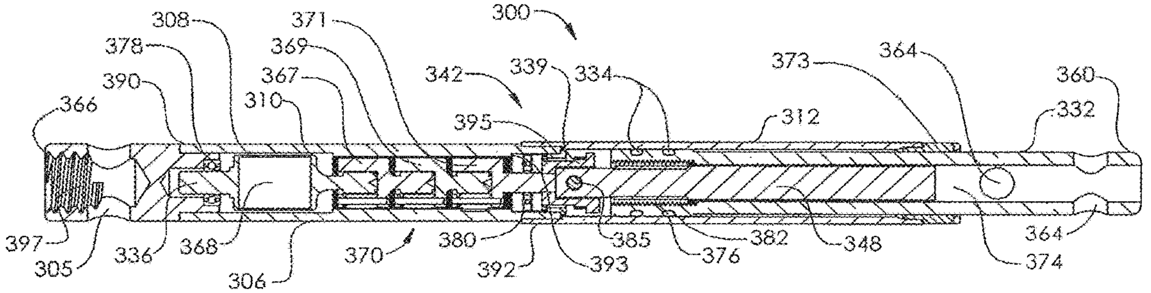
FIG. 18 illustrates a sectional view of the non-invasively adjustable wedge osteotomy device of FIG. 17.
Figure 19:
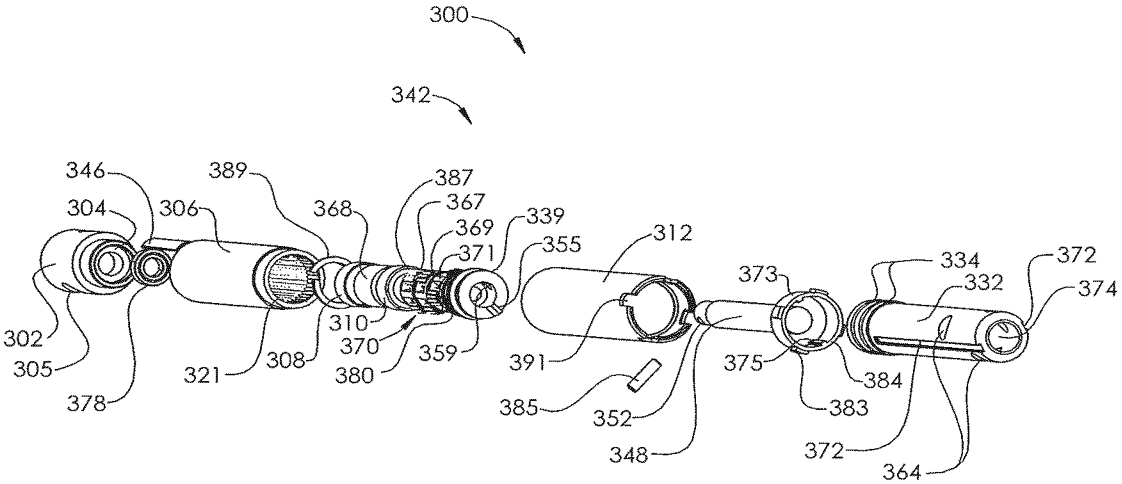
FIG. 19 illustrates an exploded view of the non-invasively adjustable wedge osteotomy device of FIG. 17.

FIGS. 17-19 illustrate a non-invasively adjustable wedge osteotomy device 300 comprising a magnetically adjustable actuator 342 having a first end 326 and a second end 328. An inner shaft 332 having a cavity 374 is telescopically coupled within an outer housing 330, which comprises a distraction housing 312 and a gear housing 306. At least one transverse hole 305 passes through an end cap 302 located at the first end 326 of the magnetically adjustable actuator 342. The end cap 302 may be sealably secured to the gear housing 306 by a circumferential weld joint 390. A second weld joint 392 sealably secures the distraction housing 312 to the gear housing 306. One or more transverse holes 364 pass through the inner shaft 332. The one or more transverse holes 364 and the at least one transverse hole 305 allow passage of at least one locking screw. Some embodiments use only one transverse hole 364 and one transverse hole 305 in order to better allow rotational play between the magnetically adjustable actuator 342 and the locking screws as the magnetically adjustable actuator 342 is adjusted. One or more longitudinal grooves 372 in the outer surface of the inner shaft 332 engage in a keyed manner with protrusions 375 in an anti-rotation ring 373 which engages undercuts within end of the distraction housing 312 at a flat edge 384 of the anti-rotation ring 373. One or more guide fins 383 in the anti-rotation ring 373 can keep the anti-rotation ring 373 rotationally static within cuts 391 in the distraction housing 312.

The contents of the magnetically adjustable actuator 342 are protected from body fluids by one or more o-rings 334 which reside within circumferential grooves 382 in the inner shaft 332, dynamically scaling along the inner surface of the distraction housing 312. The inner shaft 332 is driven axially with respect to the outer housing 330 by a lead screw 348 which is turned by a cylindrical radially poled magnet 368. The cylindrical radially poled magnet 368 is bonded within a first magnet housing 308 and a second magnet housing 310 and is rotatably held at a pin 336 on one end by a radial bearing 378, which directly engages the counterbore 304 of the end cap 302. The second magnet housing 310 outputs into a first stage 367 of three planetary gear stages 370. The planet gears 387 of the three planetary gear stages 370 turn within inner teeth 321 within the gear housing 306. The first stage 367 outputs to a second stage 369, and the second stage 369 outputs to a third stage 371. The third stage 371 is coupled to the lead screw 348 by a locking pin 385, which passes through holes 352 in both the output of the third stage 371 and in the lead screw 348. A lead screw coupler 339 is also held to the lead screw 348 by the pin 385, which passes through a hole 359. The lead screw 348 threadingly engages with a nut 376 which is bonded within the cavity 374 of the inner shaft 332. Each planetary gear stage 370 incorporates a 4:1 gear ratio, producing an overall gear ratio of 64:1, so that 64 turns of the cylindrical radially poled magnet 368 cause a single turn of the lead screw 348. A thrust bearing 380, is held loosely in the axial direction between ledges in the gear housing 306. The lead screw coupler 339 includes a ledge 355, which is similar to an opposing ledge (not shown) at the base of the lead screw 348. If the inner shaft 332 is retracted to the minimum length, the ledge at the base of the lead screw 348 abuts the ledge 355 of the lead screw coupler, assuring that the lead screw 348 cannot be jammed against the nut with too high of a torque. The thrust bearing 380 is held between a ledge 393 in the gear housing 306 and an insert 395 at the end of the gear housing 306. The thrust bearing 380 serves to protect the cylindrical radially poled magnet 368, the planetary gear stages 370, the magnet housings 308 and 310, and the radial bearing 378 from damage due to compression. A maintenance member 346 comprising a thin arc of magnetic material, such as '400 series' stainless steel, is bonded within the gear housing 306, adjacent to the cylindrical radially poled magnet 368, and can attract a pole of the cylindrical radially poled magnet 368, in order to minimize the chance of the cylindrical radially poled magnet 368 turning when not being adjusted by the external adjustment device 1180, for example during patient movement.

The non-invasively adjustable wedge osteotomy device 300 has the capability to increase or decrease its length at least about three millimeters in each direction in one embodiment, and about nine millimeters in each direction in another embodiment. The non-invasively adjustable wedge osteotomy device 300 can achieve a distraction force of 240 pounds when the magnetic handpiece 1178 of the external adjustment device 1180 is placed so that the magnets 1186 are about one-half inch from the cylindrical radially poled magnet 368. The majority of the components of the non-invasively adjustable wedge osteotomy device may be made from Titanium or Titanium alloys such as Titanium-6A1-4V, Cobalt Chromium. Stainless Steel or other alloys. When implanted, the non-invasively adjustable wedge osteotomy device 300 may be inserted by hand or may be attached to an insertion tool (for example a drill guide). An interface 366 comprising an internal thread 397 is located in the end cap 302 for reversible engagement with the male threads of an insertion tool. Alternatively, these features may be located on the end 360 of the inner shaft 332. Additionally a detachable tether may be attached to either end of the non-invasively adjustable wedge osteotomy device 300, so that it may be easily removed if placed incorrectly.

Figure 20:
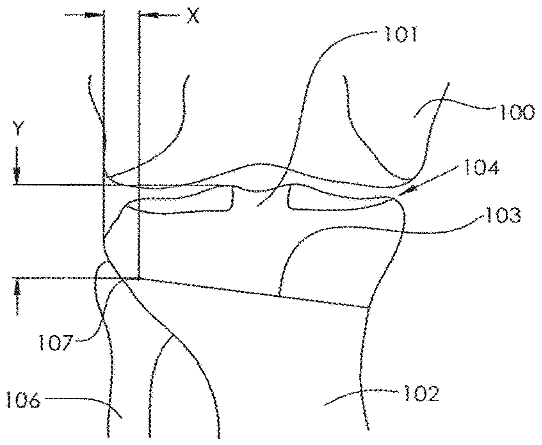
FIGS. 20-27 illustrate a method of implanting and operating a non-invasively adjustable wedge osteotomy device for maintaining or adjusting an angle of an opening wedge osteotomy of the tibia of a patient.
Figure 21:
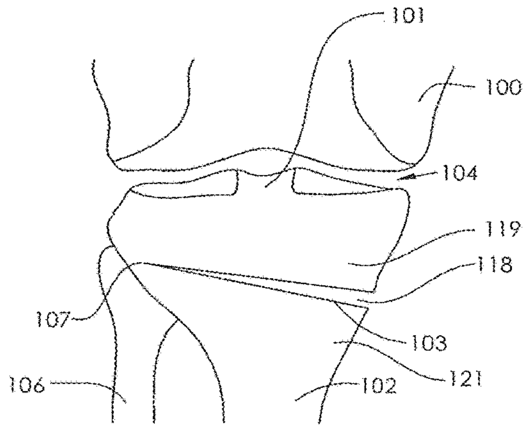

FIGS. 20 through 27 illustrate a method of implanting and operating a non-invasively adjustable wedge osteotomy device 125 for changing an angle of the tibia of a patient. In FIG. 20, a front view of the right knee joint 104 of a patient with osteoarthritis of the knee is shown, including the femur 100, tibia 102 and fibula 106. The non-invasively adjustable wedge osteotomy device 125 can be placed towards the medial side of the tibia 102 (away from the fibula 106). The bone of the tibia 102 is thus prepared to allow a non-central placement of the non-invasively adjustable wedge osteotomy device. An incision is made in the skin at a medial side of the tibia 102 and an open wedge osteotomy 118 is made in relation to a hinge point 107, by creating a first cut 103, for example with an oscillating saw, and opening the open wedge osteotomy 118, as seen in FIG. 21. A typical location for the hinge point 107 may be described by the distances X and Y in FIG. 20. In some embodiments, X=10 mm and Y=15 mm. At the hinge point, it is common to make a small drill hole and place an apex pin, for example an apex pin with a diameter of about 3 mm to about 4 mm. The open wedge osteotomy 118 now separates a first portion 119 and second portion 121 of the tibia 102.

Figure 22:
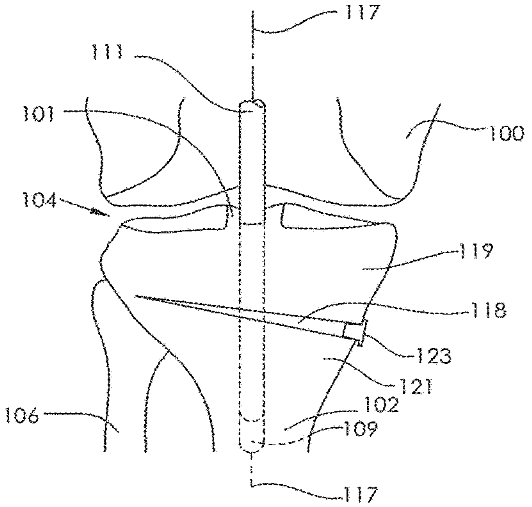
Figure 23:
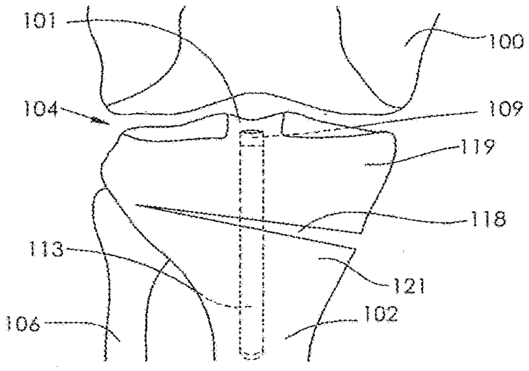
Figure 24:
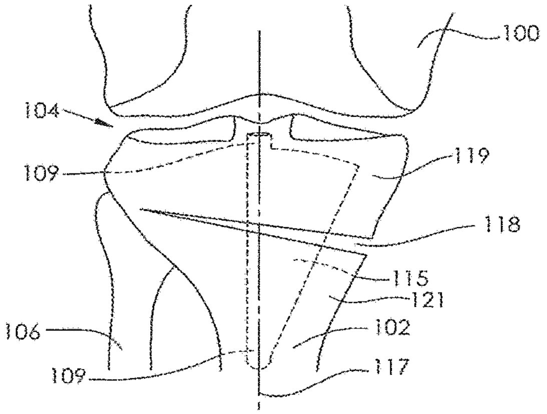
Figure 25:
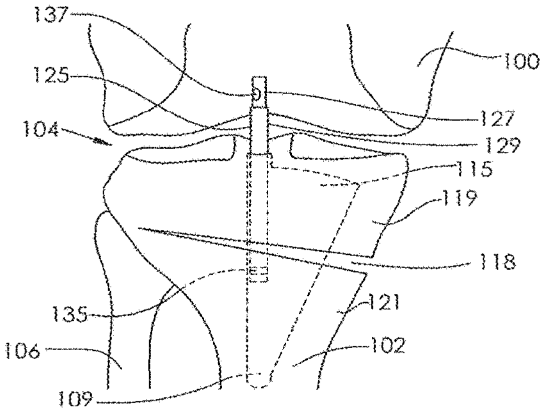

As seen in FIG. 22, an incision is made in the skin, a drill 111 is placed at the central tibial plateau 101 and a first cavity 109 having a first axis 117 is drilled from the tibial plateau 101 down the medullary canal of the tibia 102. It may be desired during this drilling step to place a temporary wedge 123 in the open wedge osteotomy 118, in order to maintain stability. A drill diameter of about 12 mm or less, or more preferably about 10 mm or less is used to create the first cavity 109. FIGS. 23 and 24 illustrate generalized steps for creating a second cavity 115. Several embodiments are represented here by an excavation device 113, which is inserted into the first cavity 109 through the opening at the tibial plateau 101. The second cavity 115 is then formed to one side of the first cavity 109, in this case the medial side. As shown in FIG. 25, after the excavation device 113 has been removed, a non-invasively adjustable wedge osteotomy device 125 having an outer housing 129 and an inner shaft 127 is inserted into the first cavity 109. In FIG. 25, the non-invasively adjustable wedge osteotomy device 125 is shown with the inner shaft 127 facing superiorly (up) on the patient, but it may desired in some situations to implant the non-invasively adjustable wedge osteotomy device 125 with the inner shaft 127 facing inferiorly (down). First transverse hole 135 and second transverse hole 137 in the non-invasively adjustable wedge osteotomy device 125 are configured for placement of bone anchors, for example locking screws.

Figure 26:
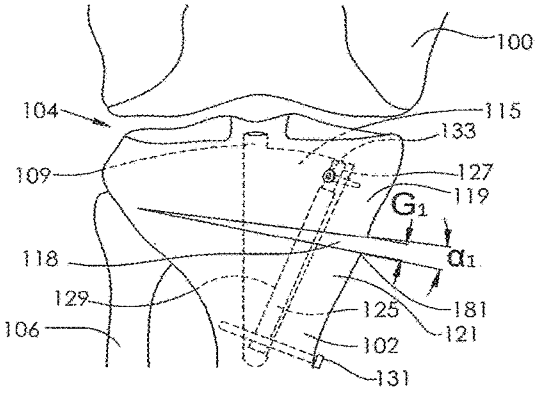
Figure 27:
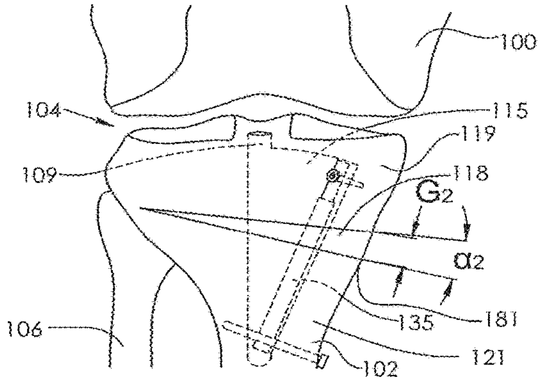

In FIG. 26, the non-invasively adjustable wedge osteotomy device 125 is then placed into the second cavity 115 and secured with a first anchor 131 through first transverse hole 135 and a second anchor 133 through second transverse hole 137. Based on calculations made from pre-surgery and/or surgery x-rays or other images, a wedge angle at is set between the first portion 119 and second portion 121 of the tibia. After post-surgical recovery, the patient may return for a dynamic imaging session (for example x-ray) during which the patient stands, and even moves the knee joint 104, in order to best confirm whether the wedge angle $\alpha$1 is allows for the optimal conformation of the knee joint 104. If, for example, at this time it is desired to increase the wedge angle $\alpha$1, the magnetic handpiece 1178 of the external adjustment device 1180 of FIG. 15 is then placed over the knee joint 104 of the patient and operated so that the inner shaft 127 is distracted from the outer housing 129, to increase to a larger wedge angle $\alpha$2 (FIG. 27). It may be desired for at least one of the anchors (for example second anchor 133) to have enough clearance in the transverse hole (for example the second transverse hole 137) so that any angulation that occurs while the non-invasively adjustable wedge osteotomy device 125 is distracted, will not put an additional bending moment on the non-invasively adjustable wedge osteotomy device 125. The dynamic imaging session may be done at a time following surgery when swelling has decreased, but before bone consolidation is significant. This period may be approximately one to two weeks following surgery. If an adjustment is made (increase or decrease), an additional dynamic imaging session may be performed, for example, a week later. The non-invasively adjustable wedge osteotomy device 125 is supplied so that it can be either lengthened or shortened, in other words, so that the angle of the open wedge osteotomy 118 may be subsequently increased or decreased, depending on the determination of the desired correction.

An alternative manner of quantifying the amount of opening of the open wedge osteotomy 118, is to measure, for example via radiography, the gap G1, G2 at the medial edge 181 of the open wedge osteotomy 118. At the typical range of angles of open wedge osteotomies 118, and the typical range of patient tibia 102 sizes, the gap G1, G2, in millimeters tends to approximate the wedge angle $\alpha$1, $\alpha$2 in degrees. For example, G1 (mm)≈$\alpha$1 (°); G2 (mm)≈$\alpha$2 (°). It is expected that, assuming correction is required, productive lengthening will be done at a rate in the range of about 2 mm gap (G) increase per day or less. Gap increase rate (GIR) may be defined as the change in gap in millimeters per day. One consideration in determining the gap increase rate (GIR) to use is the pain tolerance of the patient. Some patients may tolerate a larger amount of pain, for example the pain caused by stretching of soft tissue, and thus a higher gap increase rate (GIR). Another consideration is the amount of bone growth that is occurring. One method of assessing the amount of bone growth is via radiography. The preferred gap increase rate (GIR) is that at which bone growth is occurring within the open wedge osteotomy 118, but early consolidation of the bone is not occurring (consolidation that would "freeze" the mobility of the open wedge osteotomy 118, making it unable to be opened more). It may be desired to purposely implant the non-invasively adjustable wedge osteotomy device 125 with an undersized initial gap (G0), so that an ideal gap (G1) may be gradually achieved via non-invasive adjustments. It is contemplated that over the adjustment period, a total of one to twenty or more adjustment procedures may be performed, for a total amount of about 1 mm to about 20 mm of gap (G) increase, such as during an adjustment period of one month or less. Typically, the adjustment period may span approximately ten days, involve approximately ten adjustment procedures and involve a total amount of about 5 mm to about 12 mm gap increase.

Figure 28:
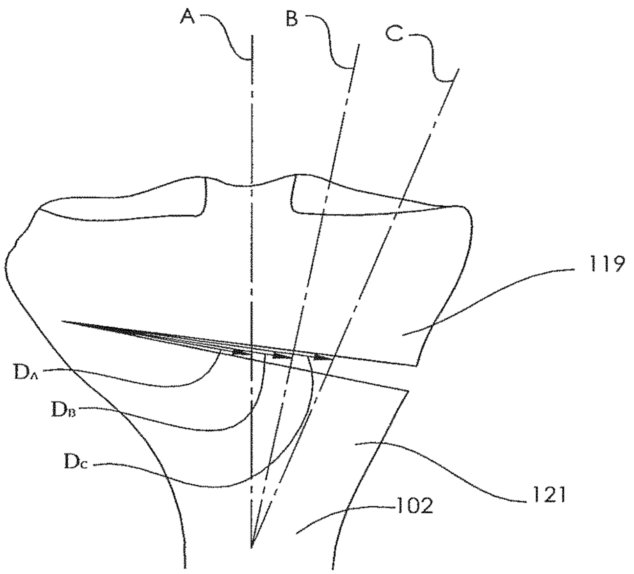
FIG. 28 illustrates distraction axes in a tibia.

By locating the non-invasively adjustable wedge osteotomy device 125 medially in the tibia, instead of near the centerline, a larger moment may be placed on the first portion 119 and second portion 121 to open the open wedge osteotomy 118 in relation to the hinge point 107. Additionally, for any particular distraction force applied by the non-invasively adjustable wedge osteotomy device 125, a larger amount of distraction may be achieved. In FIG. 28, three different distraction axes (A, B, C) are shown, representing three possible positions of the non-invasively adjustable wedge osteotomy device 125. Distraction axis A is approximately midline in the tibia 102, while distraction axis B is approximately 11° angled from the midline, and distraction axis C is approximately 22° angled from the midline. The length DB from the hinge point 107 to distraction axis B can be approximately 32% greater than the length DA from the hinge point 107 to distraction axis A. More significantly, the length DC from the hinge point 107 to distraction axis C can be approximately 60% greater than the length DA from the hinge point 107 to distraction axis A. The distraction force of the non-invasively adjustable wedge osteotomy device 125 is needed to overcome a series of resistances arrayed along the tibia due to the tethering effect of soft tissue. A placement of the non-invasively adjustable wedge osteotomy device 125 along axis C, and thus in second cavity 115 (FIG. 27), can allow for a more effective distraction of the open wedge osteotomy 118.

Figure 29:
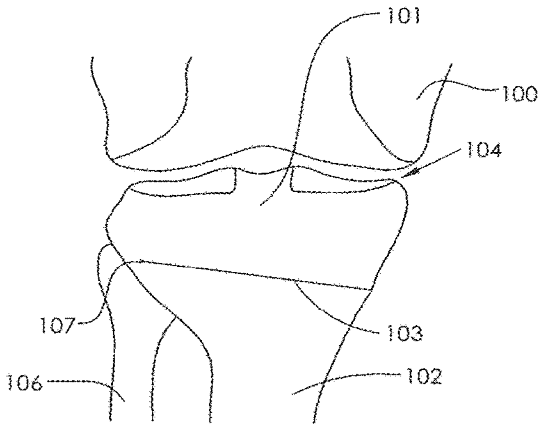
FIGS. 29-31 illustrate a method of implanting and operating a non-invasively adjustable wedge osteotomy device for maintaining or adjusting an angle of a closing wedge osteotomy of the tibia of a patient.
Figure 30:
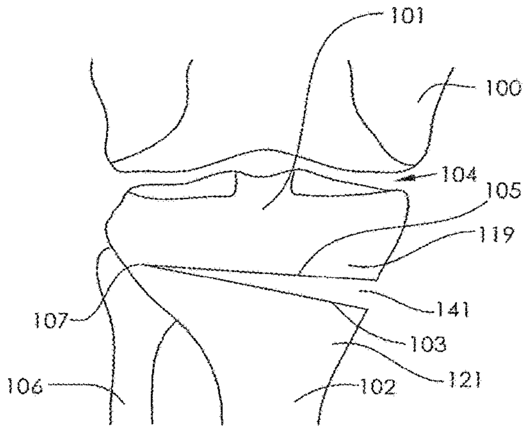
Figure 31:
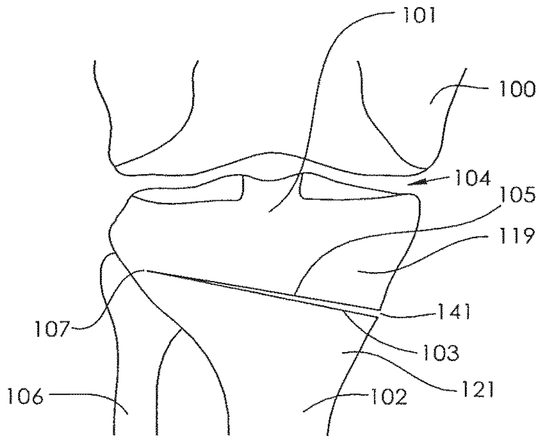

FIGS. 29 through 31 illustrate a method of implanting and operating a non-invasively adjustable wedge osteotomy device 125 for changing an angle of the tibia of a patient, but unlike the open wedge osteotomy 118 shown in FIGS. 20-27, a closing wedge osteotomy 141 is shown. In FIG. 29, the first cut 103 is made, but in FIG. 30 a second cut 105 is made and a wedge of bone is removed. The second cut 105 purposely removes slightly more bone than is needed to optimize the correction angle, and as shown in FIG. 31, the closing wedge osteotomy 141 is left with a slight gap, allowing it to be subsequently adjusted in either direction (to increase or decrease then angle). The implantation method continues by following the remaining steps described in FIGS. 22-26, and the angle of the closing wedge osteotomy 141 may be increased or decreased as described in FIG. 27.

Figure 32:
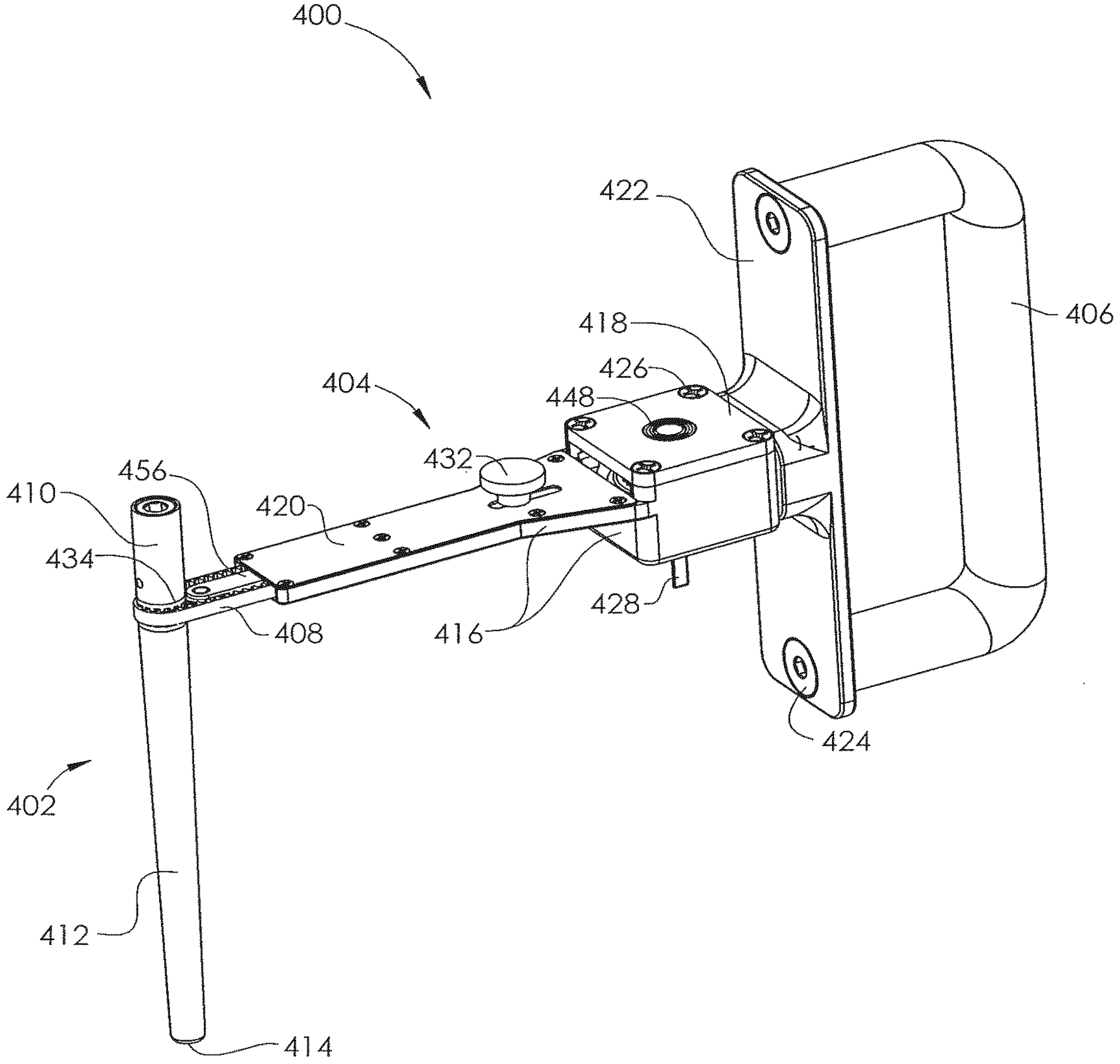
FIG. 32 illustrates a system for excavation of bone material according to a first embodiment of the present invention.
Figure 33:
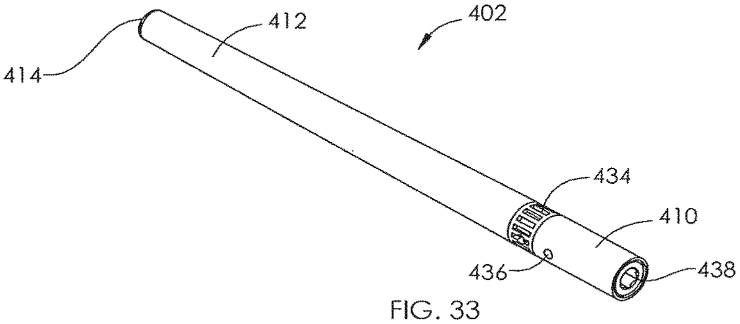
FIG. 33 illustrates a rotational cutting tool of the system of FIG. 32.
Figure 34:
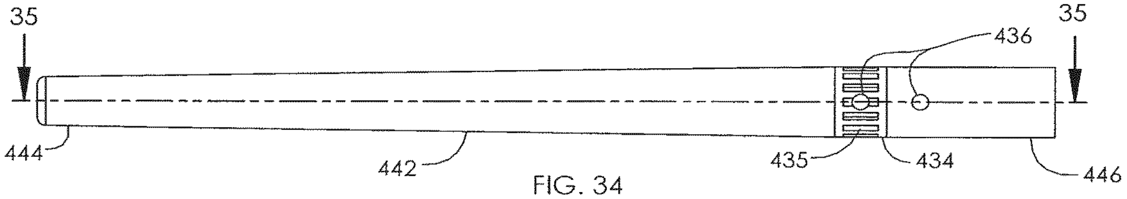
FIG. 34 illustrates a side view of the rotational cutting tool of FIG. 33.
Figure 35:
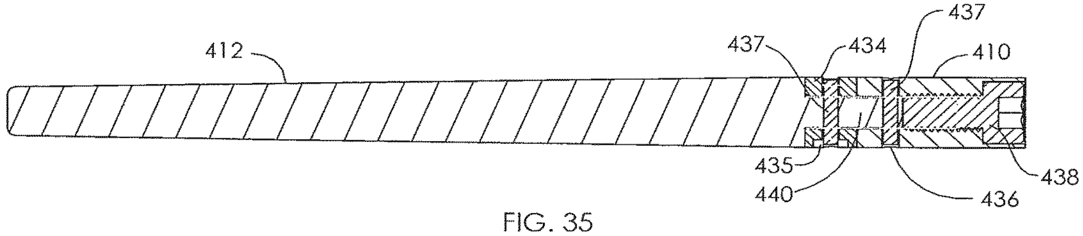
FIG. 35 illustrates a section view of the rotational cutting tool of FIG. 34, taken along line 35-35.
Figure 36:
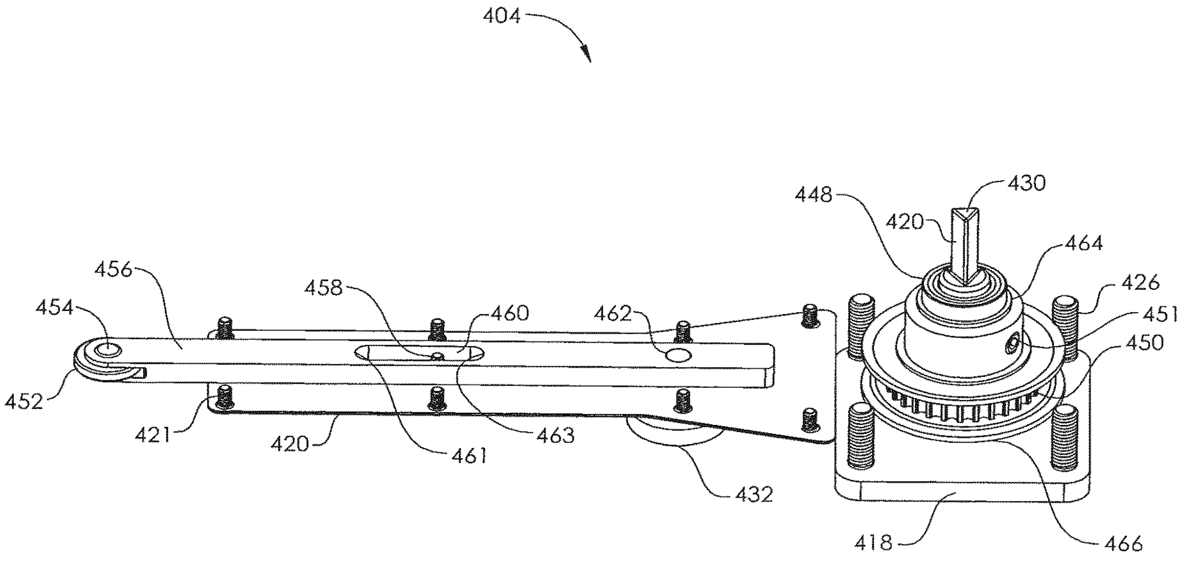
FIG. 36 illustrates a drive unit of the system of FIG. 32 with covers removed.

FIGS. 32 through 36 illustrate a first system for excavation of bone material 400. The system for excavation of bone material 400 is configured for creating a second cavity 115 as generally described in FIGS. 22 through 24. A drive unit 404 is coupled to a rotational cutting tool 402 by means of a flexible drive train 408. The rotational cutting tool 402 is an embodiment of the excavation device 113 as introduced in FIG. 23, but may also serve as the drill 111 of FIG. 22. The rotational cutting tool 402, as depicted in FIGS. 32 through 35, extends between a first end 444 and second end 446 (as shown in FIG. 34), and comprises a distal reamer 412 which is coupled to a proximal reamer 410. As shown in FIG. 35, the distal reamer 412 includes a small diameter portion 440 which inserts inside the proximal reamer 410. A circumferential engagement member 434 is held axially between the distal reamer 412 and the proximal reamer 410, and includes several cutouts 435 (FIG. 34) arrayed around its circumference, forming a pulley. The distal reamer 412, proximal reamer 410 and circumferential engagement member 434 are held together with pins 437, which are passed through holes 436, and which assure that all components rotate in unison. A cap screw 438 is secured within a female threaded internal surface of the proximal reamer 410. The distal reamer 412 further includes a taper 442 and a blunt tip 414. The outer diameter of the rotational cutting tool 402 may be about 12 mm or less, and more specifically about 10 mm or less. The outer diameter of the proximal reamer 410 may be about 9 mm and the outer diameter of the distal reamer may taper from about 9 mm to about 6.35 mm at the blunt tip 414. The drive unit 404, as best seen in FIGS. 32 and 36, comprises a drive housing 416 covered by a pulley cover plate 418 and a drive cover plate 420. Several screws 421 hold the drive cover plate 420 to the drive housing 416, and four screws 426 hold the pulley cover plate 418 to the drive housing 416. The drive housing 416 is not depicted in FIG. 36 in order to reveal more detail of the internal components. In FIG. 32, a handle 406 is coupled by screws 424 to a handle mounting plate 422 which in turn is removably attached to the drive housing 416 (for example by screws or a clip).

Figure 37:
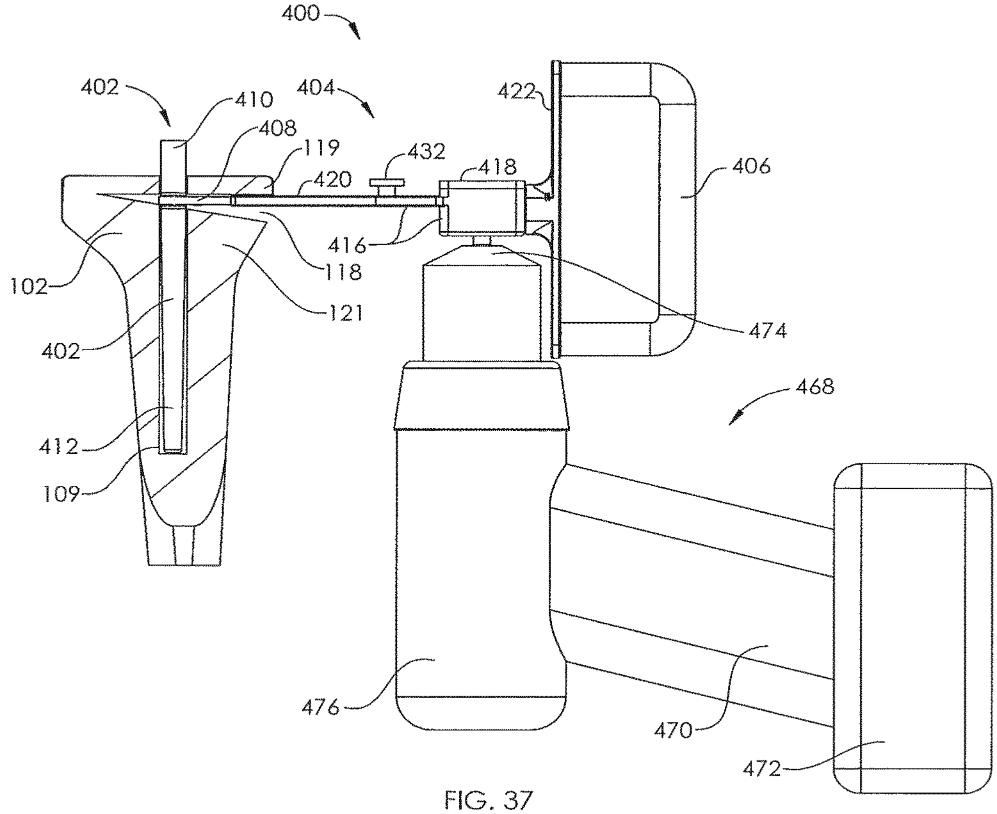
FIG. 37 illustrates the system of FIG. 32 in place within a tibia.
Figure 38:
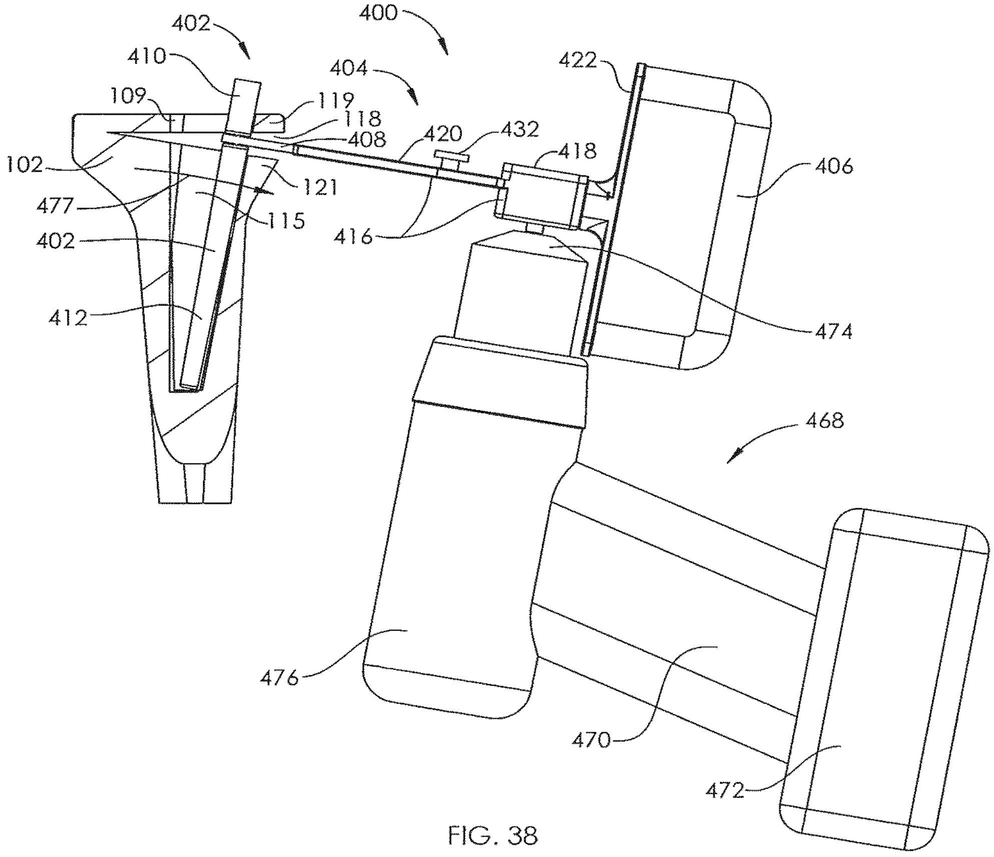
FIG. 38 illustrates the system of FIG. 32 after removing bone material from the tibia.

A shaft 428 (FIG. 36) having a keyed end 430, is configured for removeably coupling to an electric drill unit 468 (FIGS. 37 and 38). A large pulley 450 is attached to the shaft 428 with a set screw 451 so that rotation of the shaft 428 by the electric drill unit 468 causes rotation of the large pulley 450. The shaft 428 and large pulley 450 are held between two ball bearings 448 (lower ball bearing not visible), and a shim washer 464 and wave washer 466 are located on either side of the large pulley 450 in order to control the amount of axial play. A roller wheel 452 is rotatably attached to the end of a roller wheel slide 456 with a pin 454. The roller wheel slide 456 is able to slide axially within the drive housing 416 and drive cover plate 420 with the loosening of a thumb screw 432, whose threaded shaft engages with internal threads 462 on the roller wheel slide 456. The roller wheel slide 456 may be secured by tightening the thumb screw 432 so that it will not slide during use. A longitudinal slit 460 in the roller wheel slide 456 controls the total amount of axial sliding by providing a first end 461 and a second end 463 which abut a stop 458.

The flexible drive train 408 comprises a small timing belt, for example an about 3 mm wide Kevlar® or fiberglass reinforced polyurethane belt having a slippage torque of greater than 10 inch-ounces when used with the large pulley 450 or the circumferential engagement member 434. One potential example slippage torque for is 13 inch-ounces. The teeth of the flexible drive train may be located at a pitch of two millimeters. FIG. 37 shows the drive unit 404 of the System for excavation of bone material 400 coupled to the electric drill unit 468. The electric drill unit 468 includes a motor housing 476, a handle 470 and a battery pack 472. The handle may include any number of interfaces known in the art for turning the electric drill unit 468 on or off, or controlling the speed. In some embodiments, the electric drill unit 468 may plug directly into a standard power source instead of having the battery pack 472. The keyed end 430 of the shaft 428 is coupled to a shaft coupler 474 of the electric drill unit 468.

In FIG. 37, the first cavity 109 having been created, the flexible drive train 408 is inserted through the medial incision and into the open wedge osteotomy 118, between first portion 119 and second portion 121 of the tibia. The rotational cutting tool 402 is then placed down the first cavity 109 of the tibia 102 so that the flexible drive train 408 wraps around the circumferential engagement member 434 of the rotational cutting tool 402. With the thumb screw 432 loose, the desired amount of tension in the flexible drive train 408 is adjusted and then the thumb screw 432 is tightened. At this desired tension, the teeth of the flexible drive train 408 should engage well within the cutouts 435 (FIG. 34) of the circumferential engagement member 434 and the roller wheel 452 should rotatably contact the outer surface of the circumferential engagement member 434, stabilizing it. The electric drill unit 468 is operated, causing the large pulley 450 of FIG. 36 to rotate the flexible drive train 408, and thus rotate the rotational cutting tool 402 via engagement with the circumferential engagement member 434 (FIG. 34). The large pulley 450 can be twice the diameter of the circumferential engagement member 434, therefore causing the rotational cutting tool 402 to spin at one-half the speed of the output of the electric drill unit 468. Other ratios are also within the scope of this invention. It may be desired to control the rotational speed of the rotational cutting tool 402 in order to minimize heating of the bone surrounding the bone material being cut, and thus limit damage to the bone that may impede normal growth during the healing process. While the rotational cutting tool 402 is rotated by the drive unit 404. The handle 406 is pulled causing the rotational cutting tool 402 to cut a second cavity 115 following path 477 (FIG. 38). The proximal reamer 410 cuts within first portion 119 of the tibia 102 and the distal reamer 412 cuts within the second portion 121 of the tibia 102. After the second cavity 115 is created, the thumb screw 432 is loosened and tension on the flexible drive train 408 is at least partially reduced. The rotational cutting tool 402 is then removed and the flexible drive train 408 is pulled out of the open wedge osteotomy 118. A tether line may be attached to the rotational cutting tool 402, for example via the cap screw 438, to apply tension and thus aid removal. A swivel joint may further be included between the tether line and the rotational cutting tool 408 in order to keep the tether line from being twisted.

Figure 39:
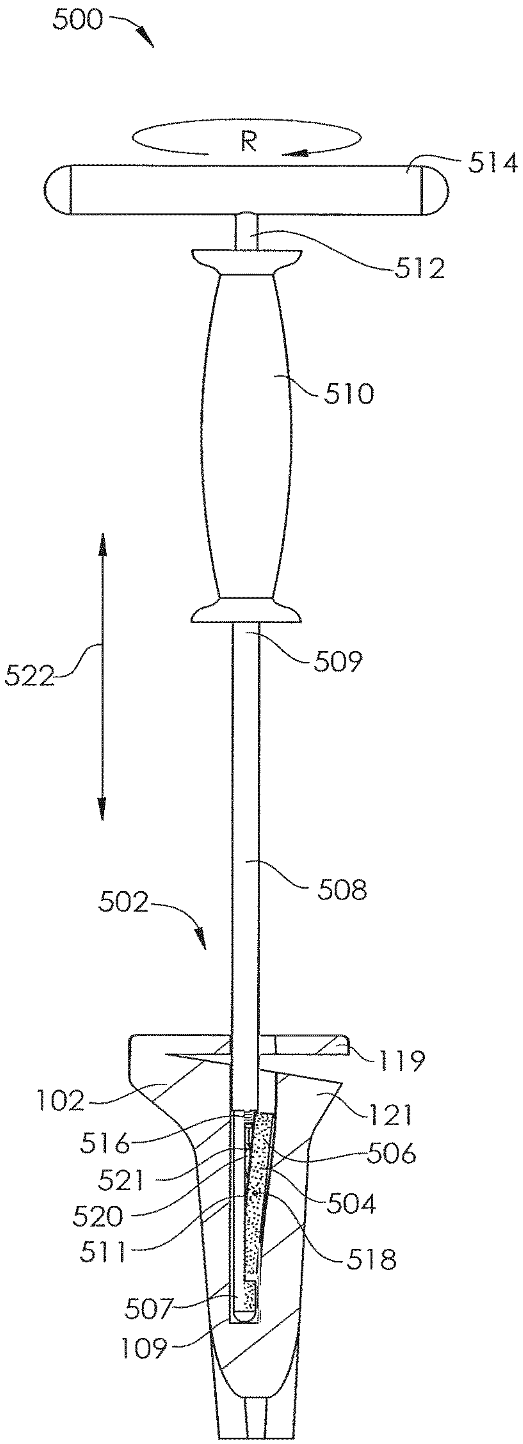
FIG. 39 illustrates a system for excavation of bone material according to a second embodiment of the present invention in place within the tibia.
Figure 40:
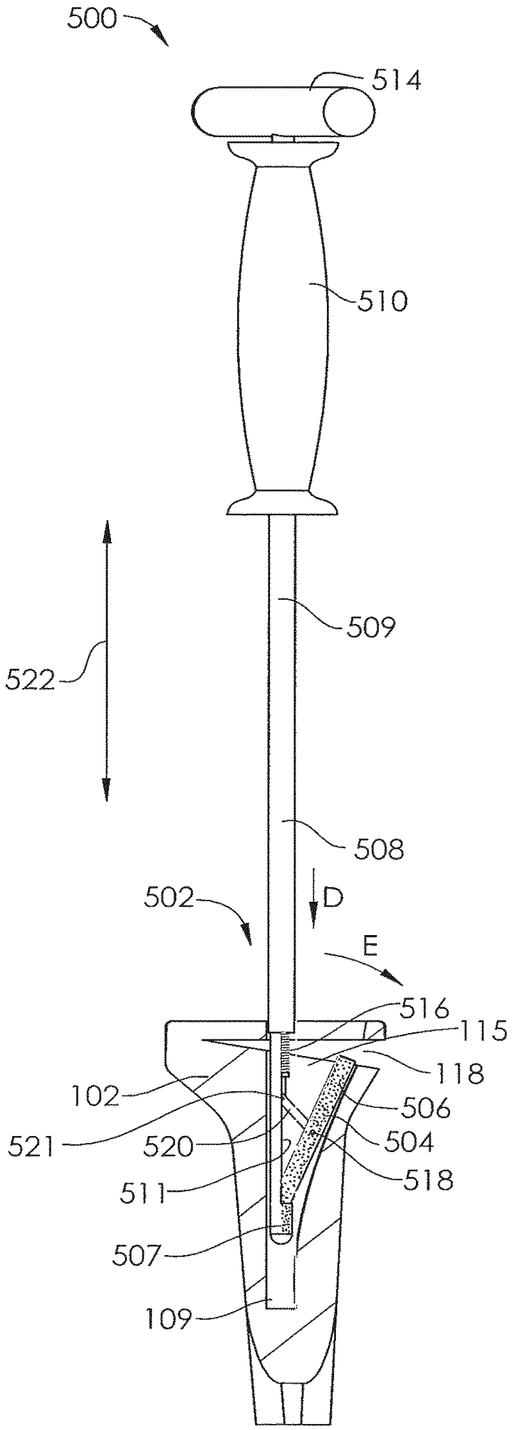
FIG. 40 illustrates the system of FIG. 39 in an expanded configuration within the tibia.
Figure 41:
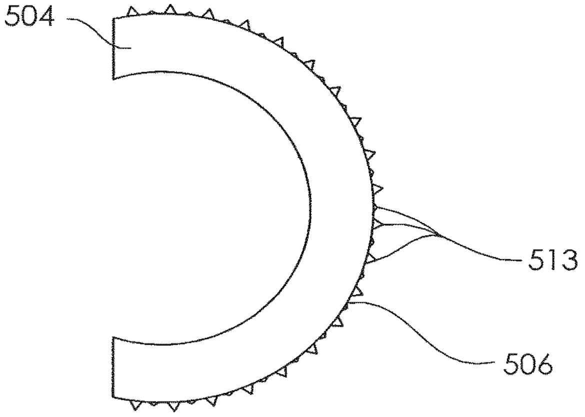
FIG. 41 illustrates an end view of an arm having an abrading surface as part of an excavation device of the system of FIG. 39.

FIG. 39-41 illustrate a second system for excavation of bone material 500. The system for excavation of bone material comprises an excavation device 502 having a hollow outer shaft 508. The hollow outer shaft 508 has a distal end 507 and a proximal end 509 and is attached to an outer shaft handle 510 which is configured to be held with a single hand to stabilize or to move the excavation device 502. An adjustment member 512 having a threaded end 516 is attached to an adjustment handle 514. The threaded end 516 threadingly engages internal threads (not shown) within the hollow outer shaft 508, and turning the adjustment member 512 by manipulation of the adjustment handle 514 moves the adjustment member 512 axially in relation to the hollow outer shaft 508. The hollow outer shaft 508 has a cut away section 511 adjacent to an articulatable arm 504. The threaded end 516 is coupled to the arm 504 via a link 520. The link 520 connects to the arm 504 at a first pivot point 518, and the link 520 connects to the threaded end 516 of the adjustment member 512 at a second pivot point 521 (as seen in FIG. 40). Rotating the adjustment handle 514 in a rotational direction R in relation to the hollow outer shaft 508 and outer shaft handle 510 causes adjustment member 512 to move in direction D in relation to the hollow outer shaft 508, and causes the arm 504 to expand in path E in relation to the hollow outer shaft 508.

The arm 504 comprises an abrading surface 506 for removing bone material. As seen in FIG. 41, the arm 504 may be an elongate member having a semi-cylindrical cross-section, and the abrading surface 506 may comprise a rasp, covered with several sharp projections 513. FIG. 39 shows the excavation device 502 placed within a first cavity 109 made within a tibia 102. In order to create a second cavity 115 to one side of the first cavity 109, the operator grips the outer shaft handle 510 with one hand and the adjustment handle 514 with the other hand, and begins moving the system for excavation of bone material 500 in a back and forth motion 522, while slowly turning the adjustment handle 514 in rotational direction R. As bone material is removed, the arm 504 is able to be expanded more and more along path E (FIG. 40) as the adjustment handle 514 is turned in rotational direction R and the system for excavation of bone material 500 is moved in a back and forth motion 522. The culmination of this step is seen in FIG. 40, with the second cavity 115 created in the first portion 119 and the second portion 121 of the tibia 102. At the completion of this step, the adjustment handle is turned in an opposite rotational direction than rotational direction R, thus allowing the arm 504 to collapse, and the excavation device 502 to be removed from the tibia 102.

Figure 44:
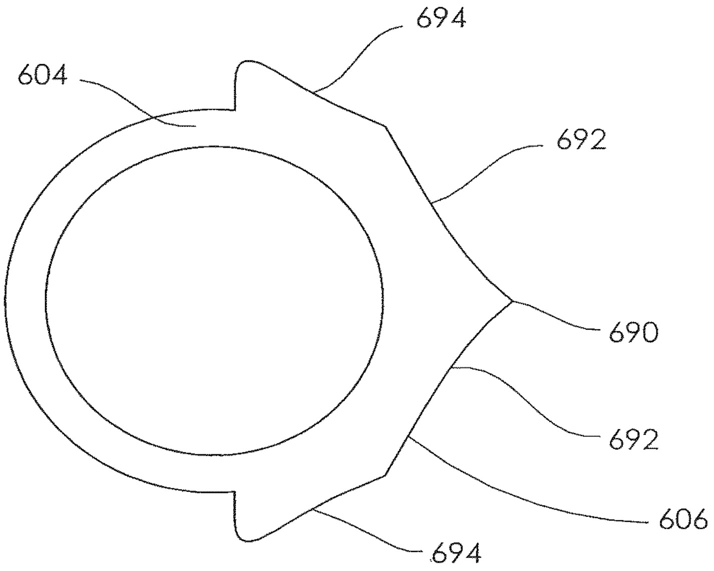
FIG. 44 illustrates an end view of an arm having a compaction surface as part of an excavation device of the system of FIG. 42.
Figure 42:
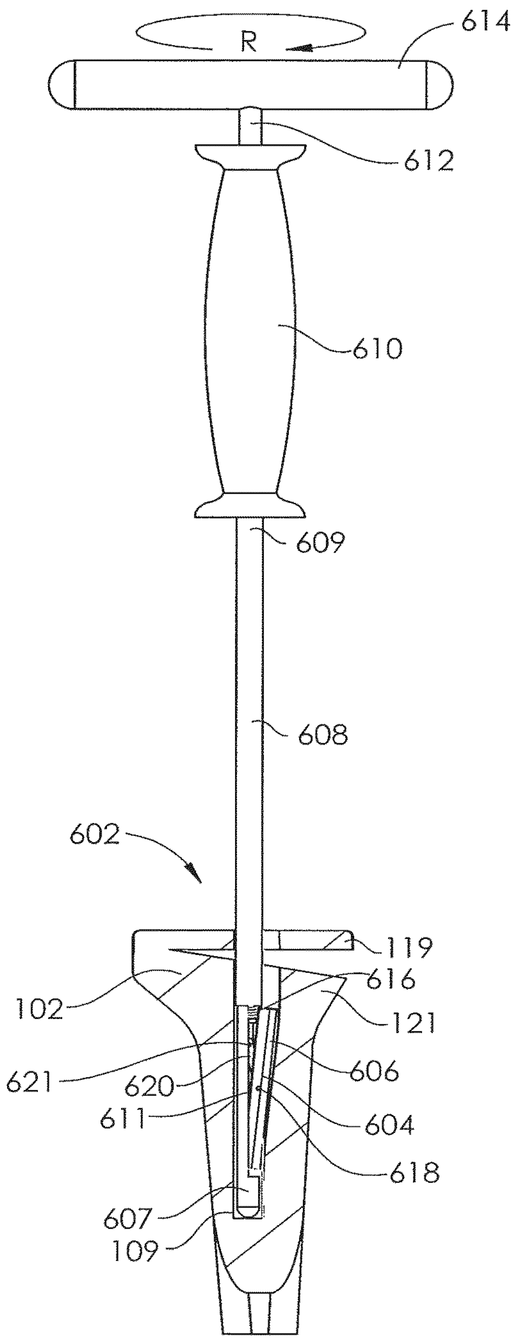
FIG. 42 illustrates a system for excavation of bone material according to a third embodiment of the present invention in place within the tibia.
Figure 43:
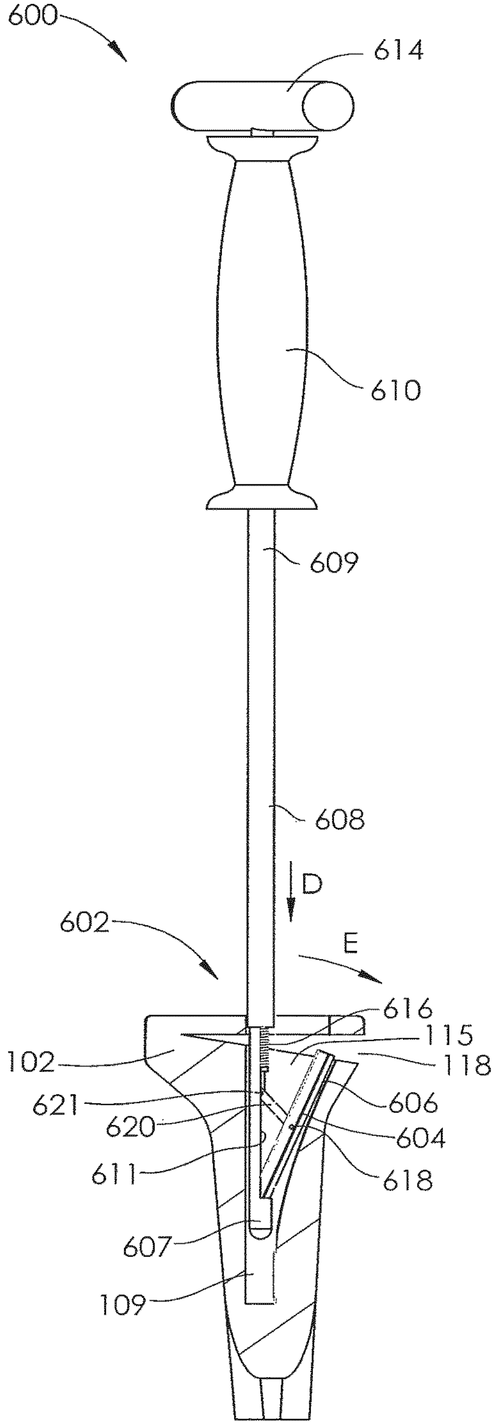
FIG. 43 illustrates the system of FIG. 42 in an expanded configuration within the tibia.

FIG. 42-44 illustrate a third system for excavation of bone material 600. The system for excavation of bone material 600 comprises an excavation device 602 having a hollow outer shaft 608. The hollow outer shaft 608 has a distal end 607 and a proximal end 609 and is attached to an outer shaft handle 610 which is configured to be held with a single hand to stabilize or to move the excavation device 602. An adjustment member 612 having a threaded end 616 is attached to an adjustment handle 614. The threaded end 616 threadingly engages internal threads (not shown) within the hollow outer shaft 608, and turning the adjustment member 612 by manipulation of the adjustment handle 614 moves the adjustment member 612 axially in relation to the hollow outer shaft 608. The hollow outer shaft 608 has a cut away section 611 adjacent to an articulatable arm 604. The threaded end 616 is coupled to the arm 604 via a link 620. The link 620 connects to the arm 604 at a first pivot point 618, and the link 620 connects to the threaded end 616 of the adjustment member 612 at a second pivot point 621. Rotating the adjustment handle 614 in a rotational direction R in relation to the hollow outer shaft 608 and outer shaft handle 610 causes adjustment member 612 to move in direction D in relation to the hollow outer shaft 608, and causes the arm 604 to expand in path E in relation to the hollow outer shaft 608, as seen in FIG. 43.

As seen in FIG. 44, the arm 604 comprises a compaction surface 606 for compacting cancellous bone. The arm 604 may be an elongate member having a tubular or partially tubular cross-section, and the compaction surface 606 may include a leading edge 690 for cutting a path through the cancellous bone and a first angled surface 692 extending from the leading edge 690. The first angled surface 692 serves to compact the cancellous bone, but also allows some sliding past cancellous bone as the cancellous bone moves out of the way. Similarly, a second angled surface 694 having an angle different from that of the first angled surface 692 may be configured as part of the compaction surface 606. FIG. 42 shows the excavation device 602 placed within a first cavity 109 made within a tibia 102. In order to create a second cavity 115 to one side of the first cavity 109, the operator grips the outer shaft handle 610 with one hand and the adjustment handle 614 with the other hand, and begins slowly turning the adjustment handle 614 in rotational direction R. Cancellous bone is compacted as the arm 604 is expanded more and more along path E by turning the adjustment handle 614 in rotational direction R. The culmination of this step is seen in FIG. 43, with the second cavity 115 created in the second portion 121 of the tibia 102. The excavation device 602 may be moved superiorly in the tibia 102 and the compaction may be completed within the first portion 119 of the tibia 102. At the completion of the compaction step, the adjustment handle is turned in an opposite rotational direction than rotational direction R, thus allowing the arm 604 to collapse, and the excavation device 602 to be removed from the tibia 102.

Figure 45A:
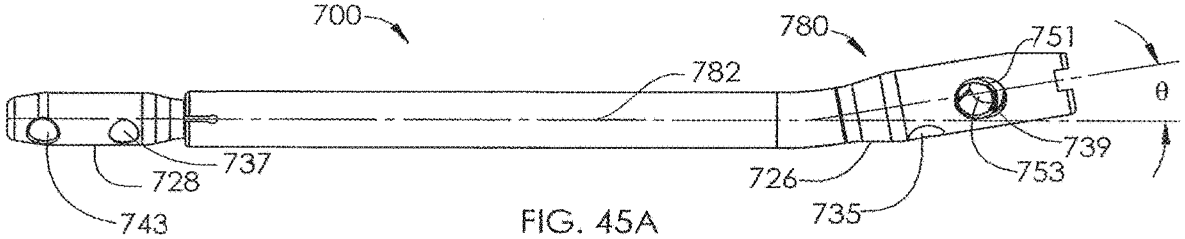
FIG. 45A illustrates a non-invasively adjustable wedge osteotomy device according to a sixth embodiment of the present invention.
Figure 45B:
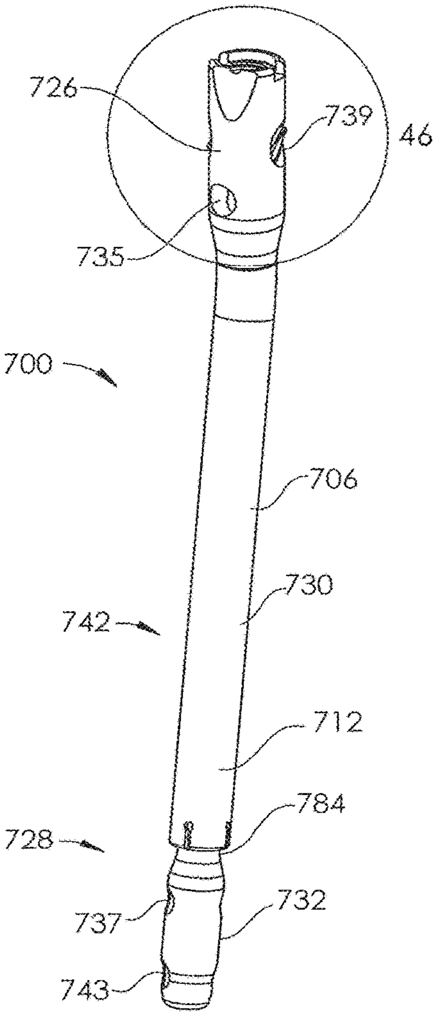
FIG. 45B illustrates the non-invasively adjustable wedge osteotomy device of FIG. 45A in a perspective view.

FIGS. 45A through 50 illustrate a non-invasively adjustable wedge osteotomy device 700. The non-invasively adjustable wedge osteotomy device 700 has a first end 726 and a second end 728, as shown in FIG. 45A, and is similar in construction to the non-invasively adjustable wedge osteotomy device 300 of FIGS. 17 through 19. However, the first end 726 of the non-invasively adjustable wedge osteotomy device 700 comprises a Herzog bend 780, in which the first end 726 projects at an angle θ. In some embodiments, the angle θ may range between about 5° and about 20°, or more specifically between about 8° to 12°, or about 10°, in relation to the central axis 782 of the non-invasively adjustable wedge osteotomy device 700. A magnetically adjustable actuator 742 comprises an inner shaft 732, telescopically disposed within an outer housing 730, the outer housing 730 further comprising a distraction housing 712 and a gear housing 706. First transverse hole 735, second transverse hole 743, third transverse hole 737 and fourth transverse hole 739 are sized for the passage of bone anchors, for example locking screws having diameters of about 3.0 mm to about 5.5 mm, and more specifically about 4.0 mm to about 5.0 mm. In some embodiments, the diameter of the outer housing 730 is between about 7.0 mm and about 9.5 mm, and more specifically about 8.5 mm. The diameter of the inner shaft 732 may also taper up to about 8.5 mm at the portion of the inner shaft 732 containing the second transverse hole 743 and third transverse hole 737. This is larger than the small-diameter portion 784 of the inner shaft 732, which telescopes within the outer housing 730, and thus this increase diameter allows the second transverse hole 743 and third transverse hole 737 to in turn be constructed with larger diameters, allowing the use of stronger, larger diameter bone screws. Likewise, the diameter of the first end 726 may taper up to about 10.7 mm in order to allow for even larger bone screws to be used. In a non-invasively adjustable wedge osteotomy device 700 having an outer housing 730 diameter of about 8.5 mm, tapering up to about 10.7 mm at the first end 726, and with an inner shaft 732 that tapers up to about 8.5 mm, it is contemplated that bone screws having diameter of about 4.0 mm will be placed through the second transverse hole 743 and the third transverse hole 737, while bone screws having a diameter of about 5.0 mm will be placed through the first transverse hole 735 and the fourth transverse hole 739. An exemplary length of the non-invasively adjustable wedge osteotomy device 700 from the extents of the first end 726 to the second end 728 is about 150 mm.

Figure 46:
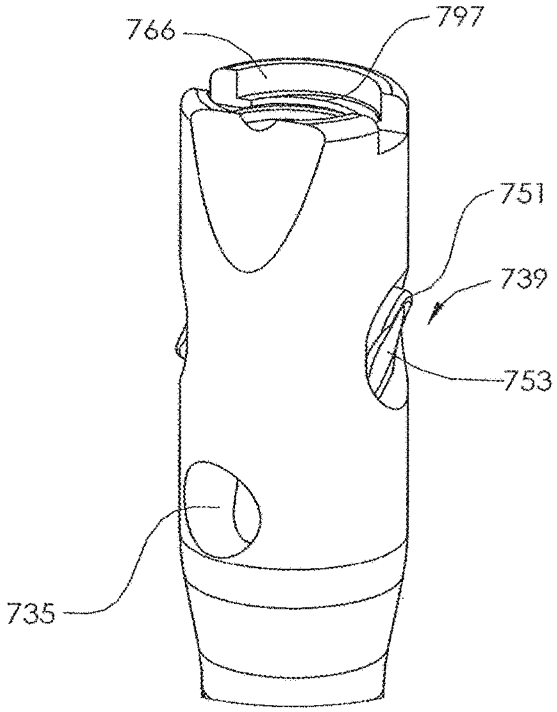
FIG. 46 illustrates a detailed view of the non-invasively adjustable wedge osteotomy device of FIG. 45B taken from within circle 46.

As seen in more detail in FIG. 46, an interface 766 at the first end 726 of the non-invasively adjustable wedge osteotomy device 700 includes internal thread 797 for reversible engagement with the male threads of an insertion tool. Examples of methods and embodiments of instruments that may be used to implant the non-invasively adjustable wedge osteotomy device 700, or other embodiments of the present invention, are described in U.S. Pat. No. 8,449,543, the disclosure of which is hereby incorporated by reference in its entirety. The fourth transverse hole 739 comprises a dynamic construction that allows some motion between a bone anchor and the non-invasively adjustable wedge osteotomy device 700 when the non-invasively adjustable wedge osteotomy device 700 is implanted and being non-invasively adjusted. A bushing 751, having substantially cylindrical outer and inner diameters resides within the fourth transverse hole 739 and has an inner diameter 753 configured to smoothly pass the shaft of a locking screw, for example a locking screw having a diameter of about 5.0 mm. In some embodiments, the bushing 751 may be constructed of metallic materials such as Titanium-6A1-4V. In other embodiments the bushing 751 may be constructed of PEEK. The bushing 751 can be angularly unconstrained, thus being able to rock or pivot within the fourth transverse hole 739.

Figure 47:
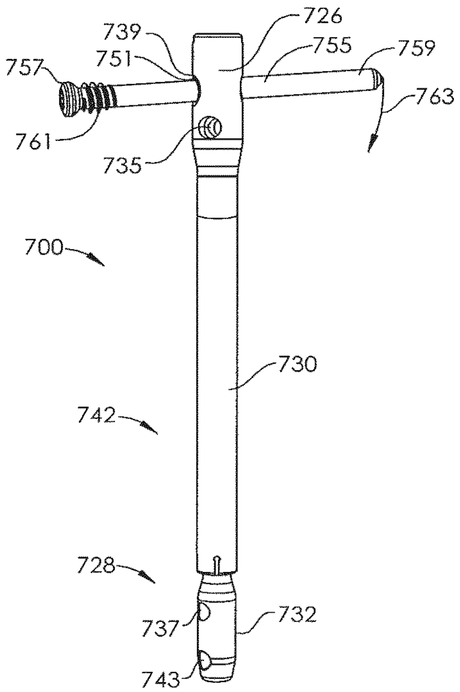
FIG. 47 illustrates the non-invasively adjustable wedge osteotomy device of FIG. 45A in a first distraction position.
Figure 48:
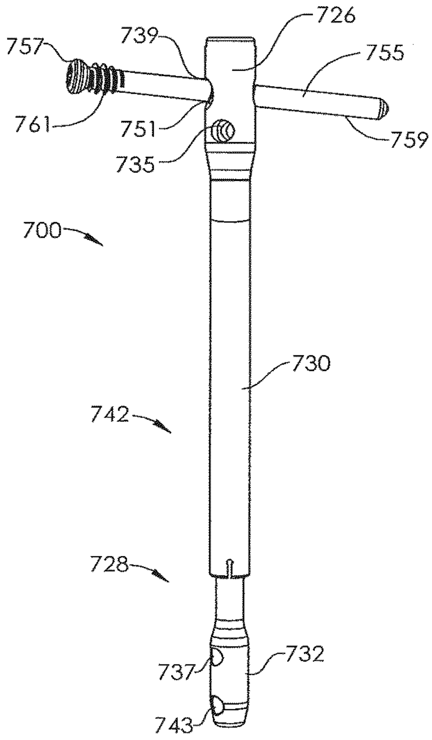
FIG. 48 illustrates the non-invasively adjustable wedge osteotomy device of FIG. 45A in a second distraction position.

FIG. 47 shows the non-invasively adjustable wedge osteotomy device 700 in a first, non-distracted state. The inner shaft 732 is substantially retracted within the outer housing 730. FIG. 48 shows the non-invasively adjustable wedge osteotomy device 700 in a partially distracted state, with a portion of the inner shaft 732 extending from the outer housing 730 (for example, after having been magnetically distracted). In addition. FIGS. 47 and 48 show two different possible positions for a bone screw 755, having a head 757, a shaft 759 and a threaded portion 761 for engaging cortical bone. The bone screw 755 is depicted rocking or pivoting along a general arcuate pathway 763. The bushing 751 may generally rock within the fourth transverse hole 739, or the bushing 751 may actually pivot upon an axis. For example, pins may extend transversely from the outer diameter of the bushing 751 at approximately the center point of its length, and attach into holes or recesses formed transversely within the fourth transverse hole 739. The words “rock” and “rocking”, as used herein, are generally intended to denote a motion that does not have a central pivot point. “Angularly unconstrained,” as used herein, is intended to denote any freedom of motion of the bushing 751 that allows angulation, not necessarily in a single plane, of the bone screw 755 in relation to the non-invasively adjustable wedge osteotomy device 700. “Angularly unconstrained,” as used herein, is intended to include both rocking and pivoting.

Figure 49:
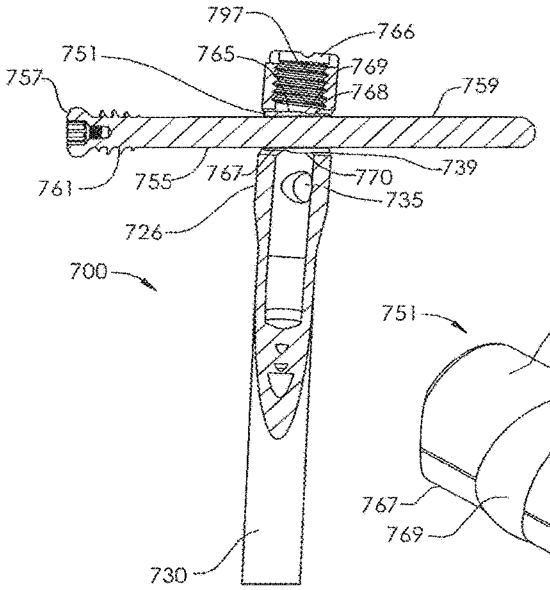
FIG. 49 illustrates a sectional view of the non-invasively adjustable wedge osteotomy device of FIG. 45A in a first distraction position.
Figure 51:
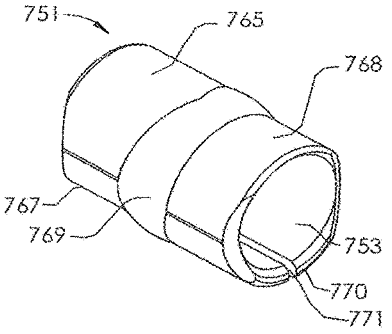
FIG. 51 illustrates a bushing of the non-invasively adjustable wedge osteotomy device of FIG. 45A.
Figure 50:
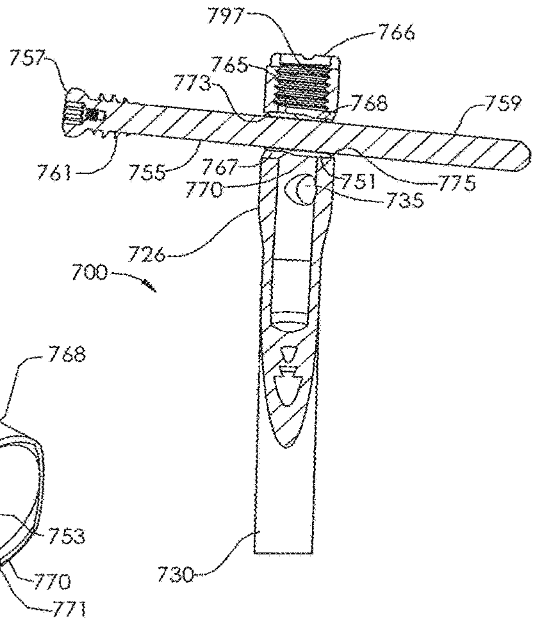
FIG. 50 illustrates a sectional view of the non-invasively adjustable wedge osteotomy device of FIG. 45A in a second distraction position.

FIGS. 49 and 50 illustrate sectional views of the bushing 751 moving in an angularly constrained manner within the fourth transverse hole 739. As seen in FIG. 51, bushing 751 comprises two large diameter extensions 765, 770 and two small diameter extensions 767, 768, separated by a transition area 769. In some embodiments, a longitudinal slit 771 along one side of the bushing 751 may be present, to allow bone screws 755 having a certain amount of outer diameter variance to fit within the inner diameter 753. In FIG. 49, the bushing 751 has not reached its extents against the fourth transverse hole 739. In contrast, FIG. 50 shows one large diameter extension 765 abutting a first point 773 within the fourth transverse hole 739, and the other large diameter extension 770 abutting a second point 775 within the fourth transverse hole 739. In addition, this longitudinal slit 771, or alternatively, external contours on the bushing 751, may fit within matching contours the fourth transverse hole 739, so that the bushing 751 cannot rotate around its cylindrical axis (in relation to the fourth transverse hole 739), but is still able to rock or pivot. The sizing of the two large diameter extensions 765, 770 and two small diameter extensions 767, 768 may be controlled, for example, so that the bushing 751 is able to rock or pivot about 15° in one direction, but about 0° in the other direction. These about 15°, for example, may be chosen to correspond to the total amount of opening of the open wedge osteotomy 118 in a particular patient. The extent of this angulation may be controlled in different models of the bushing 751. For example about 15° in one direction, about 0° in the other direction; about 10° in one direction, about 5° in the other direction; about 20° in one direction, about 0° in the other direction; and about 10° in one direction, about 10° in the other direction.

Figure 52:
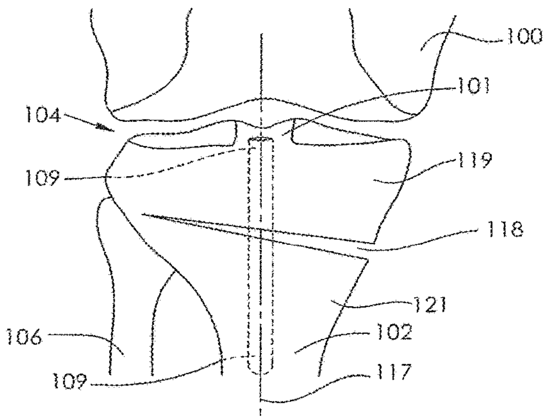
FIGS. 52-55 illustrate a method of implanting and operating the non-invasively adjustable wedge osteotomy device of FIG. 45A for maintaining or adjusting an angle of an opening wedge osteotomy of the tibia of a patient.
Figure 53:
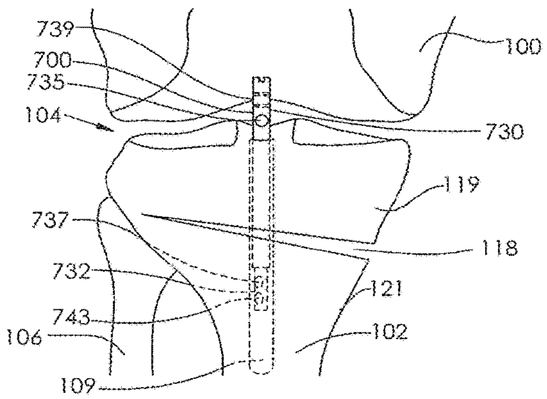
Figure 54:
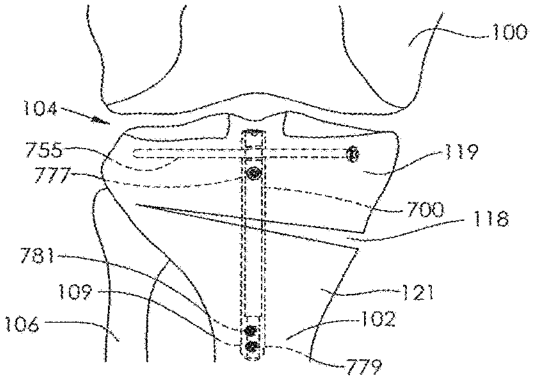
Figure 55:
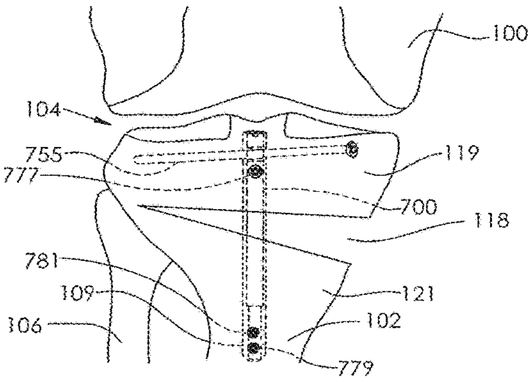

FIGS. 52-55 illustrate a method of implanting and operating the non-invasively adjustable wedge osteotomy device 700 of FIGS. 45A-51 for maintaining or adjusting an angle of an opening wedge osteotomy of the tibia of a patient. In FIG. 52, a first cavity 109, extending from a first point on the tibia 102 at the tibial plateau 101, is made. In some embodiments, the first cavity 109 can be made as shown in FIGS. 20-22. In FIG. 53, the non-invasively adjustable wedge osteotomy device 700 is inserted into the first cavity 109, the inner shaft 732 first, followed by the outer housing 730. In FIG. 54, the non-invasively adjustable wedge osteotomy device 700 is secured to the first portion 119 of the tibia 102 with a first bone screw 755 which is passed through the fourth transverse hole 739 of FIG. 45B, and a second bone screw 777 which is passed through the first transverse hole 735, of FIG. 45B. In this embodiment, only the fourth transverse hole 739 has the bushing 751 incorporated therein. A third bone screw 779 and a fourth bone screw 781 are passed through the second transverse hole 743, in FIG. 45B, and the third transverse hole 737, in FIG. 45B, respectively, and secured to the second portion 121 of the tibia 102. The non-invasively adjustable wedge osteotomy device 700 is secured within the tibia 102 so that the Herzog bend 780, of FIG. 45A, points anteriorly (e.g. towards the patellar tendon). FIG. 55 illustrates the non-invasively adjustable wedge osteotomy device 700 after having been distracted over one or more non-invasive distractions, over a period of one or more days. The angle of the open wedge osteotomy 118 has been increased as the inner shaft 732 was displaced out of the outer housing 730. The bone screw 755 has been able to change its angle in relation to the non-invasively adjustable wedge osteotomy device 700, for example, by rocking or pivoting of the bushing 751 of FIG. 49 within the fourth transverse hole 739.

Figure 56A:
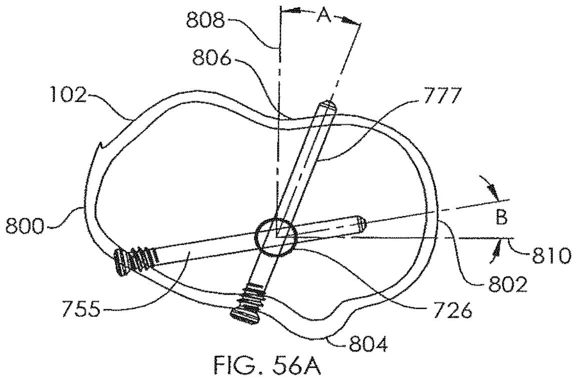
FIGS. 56A-56D illustrate bone screw configurations for the non-invasively adjustable wedge osteotomy device of FIG. 45A.
Figure 56B:
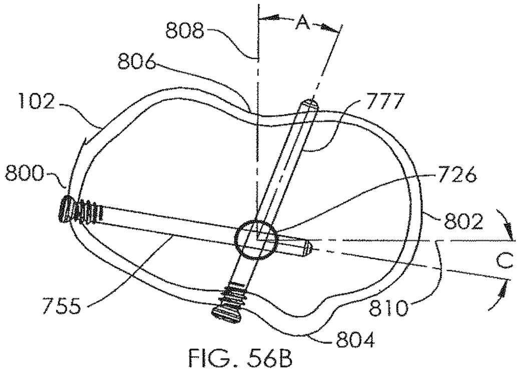
Figure 56C:
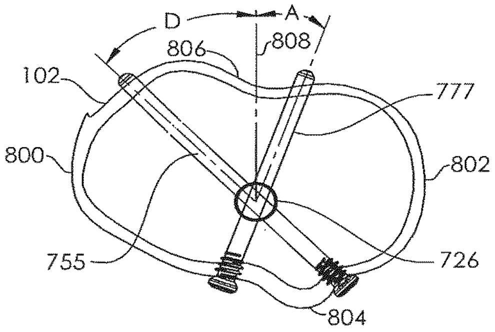
Figure 56D:
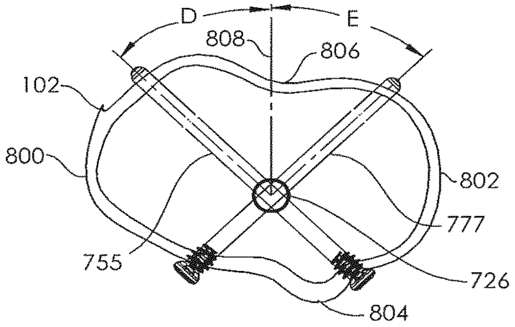

FIGS. 56A through 56D illustrate four possible bone screw configurations for securing the first end 726 of the non-invasively adjustable wedge osteotomy device 700 to the first portion 119 of the tibia 102 with the first bone screw 755 and the second bone screw 777. The medial 800, lateral 802, anterior 804 and posterior 806 portions of the tibia 102 are denoted. The medial 800 to lateral 802 orientation in FIGS. 56A through 56D is left to right respectively in each figure, while in FIGS. 52 through 55, medial was on the right and lateral was on the left. In the configuration of FIG. 56A, the first bone screw 755 is secured unicortically (through the cortex of the tibia 102 on one side only) and is at an angle of B≈10° with the medial-lateral axis 810. The second bone screw 777 is secured bicortically (through the cortex of the tibia 102 on both sides) and is at an angle of A≈20° with the anterior-posterior axis 808. In the configuration of FIG. 56B, the first bone screw 755 is secured unicortically and is at an angle of B≈10° (in the opposite direction than in FIG. 56A) with the medial-lateral axis 810. The second bone screw 777 is secured bicortically and is at an angle of A≈20° with the anterior-posterior axis 808. In the configuration of FIG. 56C, the first bone screw 755 and the second bone screw 777 are both secured bicortically. First bone screw 755 is secured at an angle of D≈45° with the anterior-posterior axis 808, and second bone screw 777 is secured at an angle of A≈20° with the anterior-posterior axis 808. In the configuration of FIG. 56D, the first bone screw 755 and the second bone screw 777 are both secured bicortically. First bone screw 755 is secured at an angle of D≈45° with the anterior-posterior axis 808, and second bone screw 777 is secured at an angle of E≈45° with the anterior-posterior axis 808.

Though not shown in FIGS. 56A through 56D, the third bone screw 779 and the fourth bone screw 781 may be secured in a number of orientations. Though shown in FIGS. 54 and 55 oriented slightly angled from the anterior-posterior plane, they may also be placed in other orientations, for example angled approximately 35° from the medial-lateral plane.

Figure 57:
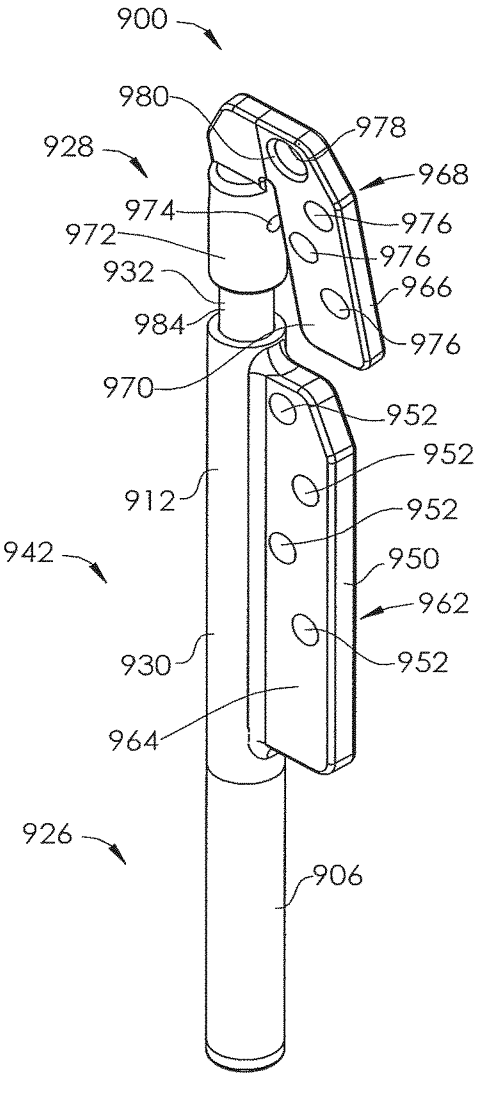
FIG. 57 illustrates a non-invasively adjustable wedge osteotomy device according to a seventh embodiment of the present invention.
Figure 58:
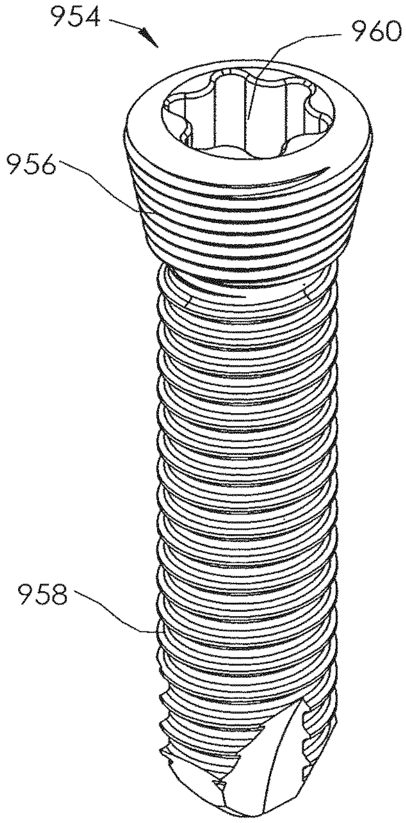
FIG. 58 illustrates a bone anchor for use with the non-invasively adjustable wedge osteotomy device of FIG. 57.

FIG. 57 illustrates a non-invasively adjustable wedge osteotomy device 900. The non-invasively adjustable wedge osteotomy device 900 comprises a magnetically adjustable actuator 942 having a first end 926 and a second end 928, and is similar in construction to the non-invasively adjustable wedge osteotomy device 300 of FIGS. 17 through 19. The second end 928 includes an inner shaft 932 having a small-diameter portion 984 which is telescopically disposed and axially distractable within an outer housing 930. The outer housing 930 comprises a distraction housing 912 and a gear housing 906. A first plate 950 extends from the outer housing 930 and is configured to be placed in proximity to an external surface of a bone, for example, the second portion 121 of a tibia 102 shown in FIG. 59. One or more anchor holes 952 are arrayed on the first plate 950, and configured for interface with corresponding bone screws. A bone screw 954 is shown in FIG. 58, and includes a threaded, tapered head 956 and a threaded shaft 958. A keyed cavity 960 couples with a driving instrument (not shown). The first plate 950 features a bone interface side 962 and a non-bone interface side 964. A second plate 966, having a bone interface side 968 and a non-bone interface side 970, extends from the inner shaft 932. The second plate 966 is coupled to the inner shaft 932 by a cap 972, and secured with a set screw 974. One or more anchor holes 976 are arrayed on the second plate 966, and configured for interface with corresponding bone screws, for example bone screw 954. Anchor hole 978 is shown having a threaded taper 980, for interfacing with the tapered head 956 of the bone screw 954.

Figure 59:
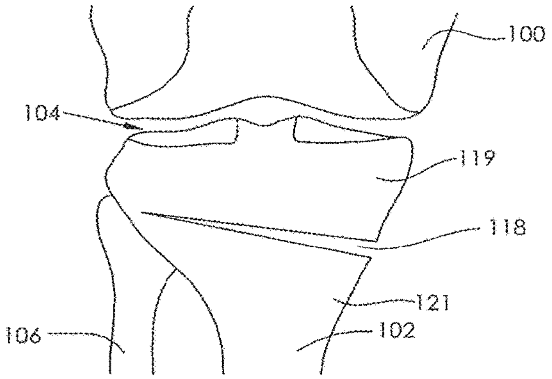
FIGS. 59-61 illustrate a method of implanting and operating the non-invasively adjustable wedge osteotomy device of FIG. 57 for maintaining or adjusting an angle of an opening wedge osteotomy of the tibia of a patient.
Figure 60:
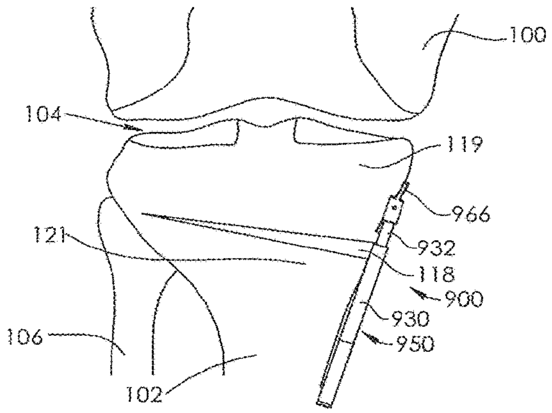
Figure 61:
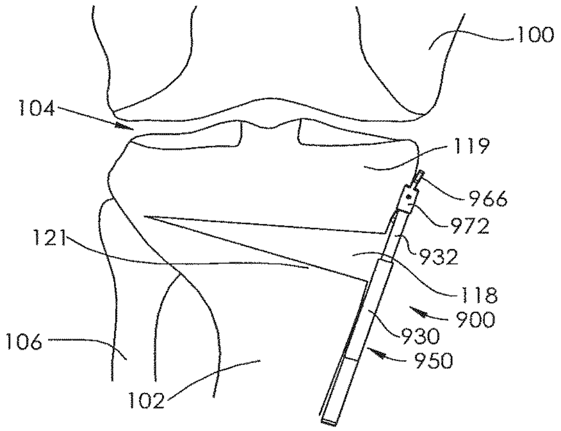

FIGS. 59-61 illustrate a method of implanting and operating the non-invasively adjustable wedge osteotomy device of FIG. 57 for maintaining or adjusting an angle of an opening wedge osteotomy of the tibia of a patient. In FIG. 59, an open wedge osteotomy 118 is made in the tibia 102. In FIG. 60, the non-invasively adjustable wedge osteotomy device 900 is placed through an incision and is secured to the tibia 102 by coupling the first plate 950 to the second portion 121 of the tibia 102 and coupling the second plate 966 to the first portion 119 of the tibia, for example with bone screws 954. FIG. 61 illustrates the tibia 102 after the non-invasively adjustable wedge osteotomy device 900 has been non-invasively distracted, for example with the external adjustment device 1180.

Figure 62:
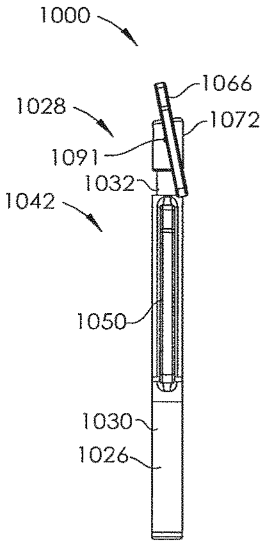
FIG. 62 illustrates a non-invasively adjustable wedge osteotomy device according to an eighth embodiment of the present invention in a first distraction position.
Figure 63:
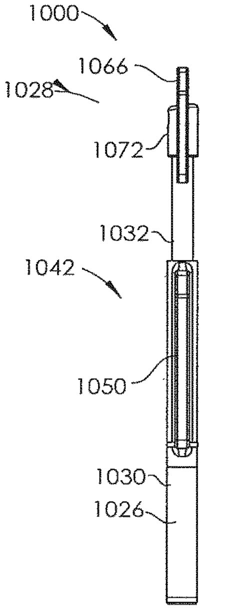
FIG. 63 illustrates the non-invasively adjustable wedge osteotomy device of FIG. 62 in a second distraction position.

FIGS. 62 and 63 illustrate a non-invasively adjustable wedge osteotomy device 1000. The non-invasively adjustable wedge osteotomy device 1000 comprises a magnetically adjustable actuator 1042 having a first end 1026 and a second end 1028, and is similar in construction to the non-invasively adjustable wedge osteotomy device 300 of FIGS. 17 through 19, and the non-invasively adjustable wedge osteotomy device 900 of FIG. 57. The magnetically adjustable actuator 1042 comprises an outer housing 1030 and an inner shaft 1032 telescopically disposed within the outer housing 1030. Like the non-invasively adjustable wedge osteotomy device 900 of FIG. 57, non-invasively adjustable wedge osteotomy device 1000 has a first plate 1050 extending from the outer housing 1030. A second plate 1066 is secured to the inner shaft 1032 by a cap 1072. The second plate 1066 is rotatably coupled to the cap 1072 at pivot point 1091, thus allowing the second plate 1066 to rotate from the position in FIG. 62 to the position in FIG. 63 along arrow 1081, for example as the inner shaft 1032 is distracted from the position in FIG. 62 to the position in FIG. 63. This allows the first portion 119 of the tibia 102 to be moved apart from the second portion 121 of the tibia 102, and thus opening the open wedge osteotomy 118, but without creating too large of a bending moment (and related frictional force increases) on the movement of the inner shaft 1032 within the outer housing 1030. In this manner, the torque supplied by the magnetic coupling of the external adjustment device 1180 of FIG. 15 will be sufficient to distract the magnetically adjustable actuator 1042. The rotatability of the second plate 1066 with relation to the rest of the non-invasively adjustable wedge osteotomy device 900 is analogous to the angularly unconstrained motion of the bushing 751 and the bone screw 755 in relation to the non-invasively adjustable wedge osteotomy device 700 of FIGS. 45A through 50.

The use of the non-invasively adjustable wedge osteotomy device 900 or the non-invasively adjustable wedge osteotomy device 1000, which do not require any removal of bone at the tibial plateau 101, may be preferred in certain patients in whom it is desired to maintain the knee joint 104 in as original a condition as possible. This may include younger patients, patients who may be able to avoid later partial or total knee replacement, or patients with deformities at the knee joint 104. It may also include small patients who have small medullary canal dimensions, in whom intramedullary devices will not fit well.

Figure 64A:
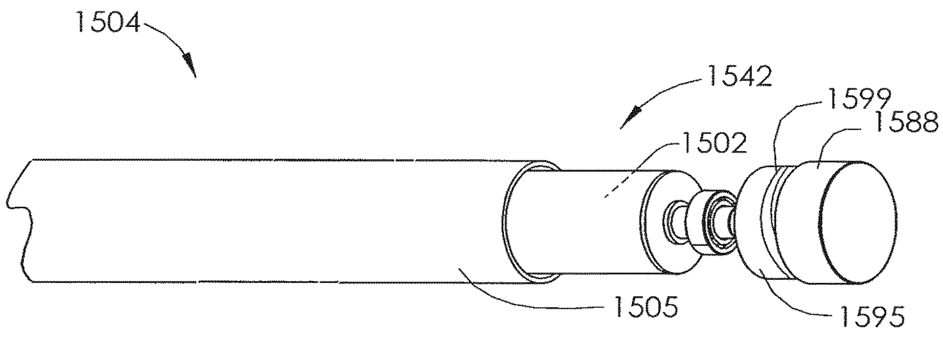
FIG. 64A illustrates a magnetically adjustable actuator of a non-invasively adjustable wedge osteotomy device according to an embodiment of the present invention during removal of a magnetic assembly.
Figure 64B:
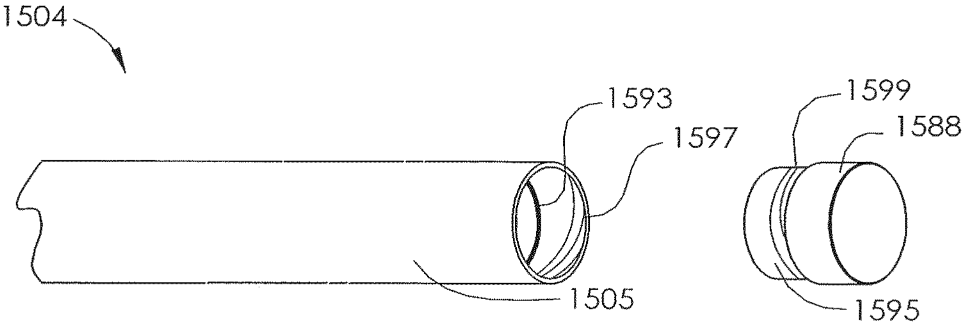
FIG. 64B illustrates the magnetically adjustable actuator of FIG. 64A after removal of a magnetic assembly.
Figure 64C:
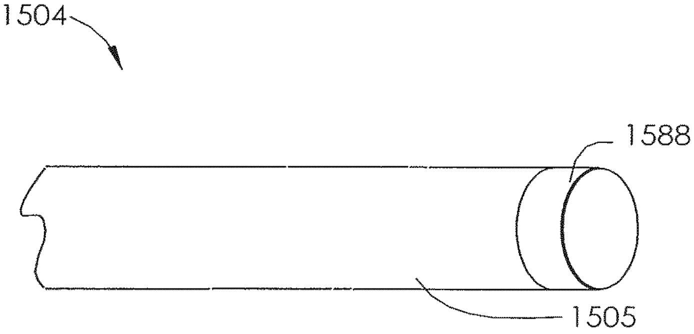
FIG. 64C illustrates the magnetically adjustable actuator FIG. 64A after replacement of an actuator housing cap.

FIGS. 64A through 64C illustrate a magnetically adjustable actuator 1504 which may be used with any of the embodiments of the present invention, and which allows for temporary or permanent removal of a rotatable magnetic assembly 1542. Subjects undergoing magnetic resonance imaging (MRI) may require that the radially-poled permanent magnet 1502 be removed prior to MRI in order to avoid an imaging artifact which may be caused by the radially-poled permanent magnet 1502. Additionally, there is a risk that an implanted radially-poled permanent magnet 1502 may be demagnetized upon entering an MRI scanner. In some embodiments, an actuator housing cap 1588 has a male thread 1599 which engages with a female thread 1597 of the outer housing 1505 of the magnetically adjustable actuator 1504. In other embodiments, a snap/unsnap interface may be used. A smooth diameter portion 1595 of the actuator housing cap 1588 is sealed within an o-ring 1593, which is held within a circumferential groove in the outer housing 1505. If at a time subsequent to the implantation of the magnetically adjustable actuator 1504 it desired to remove the rotatable magnetic assembly 1542 while leaving the rest of the implant intact, a small incision may be made in the skin of the subject in proximity to the actuator housing cap 1588, and the actuator housing cap 1588 may be unscrewed. The rotatable magnetic assembly 1542 may then be removed, as shown in FIG. 64A. FIGS. 64B and 64C show the subsequent steps of replacing the actuator housing cap 1588 onto the magnetically adjustable actuator 1504, once again sealing it with the o-ring 1593. The incision may then be closed, and the subject can undergo typical MRI scanning. If desired, after the MRI scanning, the magnetic assembly 1542 may be replaced by following a reverse method.

Figure 65A:
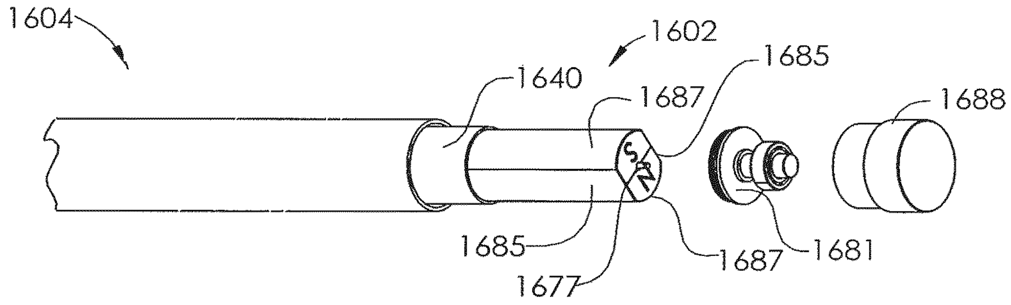
FIG. 65A illustrates a magnetically adjustable actuator of a non-invasively adjustable wedge osteotomy device according to an embodiment of the present invention prior to removal of a radially-poled permanent magnet.
Figure 65B:
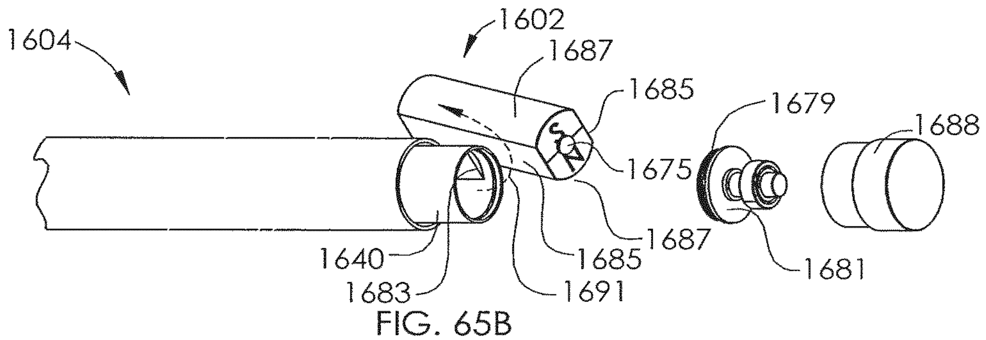
FIG. 65B illustrates the magnetically adjustable actuator of FIG. 65A during removal of the radially-poled permanent magnet.
Figure 65C:
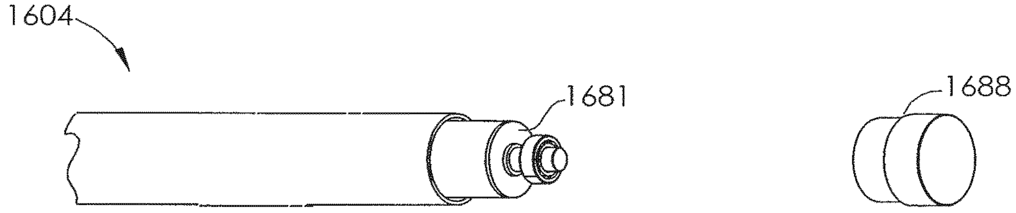
FIG. 65C illustrates the magnetically adjustable actuator of FIG. 64A after removal of the radially-poled permanent magnet and replacement of a magnetic housing cap.
Figure 65D:
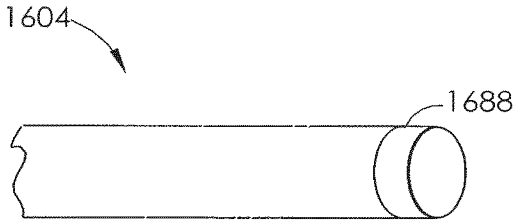
FIG. 65D illustrates the magnetically adjustable actuator of FIG. 64A after replacement of an actuator housing cap.

FIGS. 65A through 65D illustrate a magnetically adjustable actuator 1604 which may be used with any of the embodiments of the present invention, and which advantageously allows for temporary or permanent removal of the radially-poled permanent magnet 1602. An actuator housing cap 1688 attaches to and detaches from the magnetically adjustable actuator 1604 in the same manner as in the magnetically adjustable actuator 1504 of FIGS. 64A through 64C. The radially-poled permanent magnet 1602 has two radial portions 1687 and two flat portions 1685. The two flat portions 1685 fit within flat walls 1683 of a magnetic housing 1640, which allows rotation of the radially-poled permanent magnet 1602 to directly impart a torque upon the magnetic housing 1640 without the need for any adhesive or epoxy. A magnetic housing cap 1681 having an o-ring 1679 is attachable to and removable from the magnetic housing 1640. If an MRI of the subject is desired and it has been determined that the radially-poled permanent magnet 1602 should be removed, an small incision is made in the skin of the subject in proximity to the actuator housing cap 1688, and the actuator housing cap 1688 is removed. Then magnetic housing cap 1681 is removed from the magnetic housing 1640. A pull rod 1677 extends through a longitudinal hole (not shown) in the radially-poled permanent magnet 1602, extending at one end such that it may be gripped, for example by forceps or hemostats. The pull rod 1677 may have a flat base 1675 at the opposite end so that when it is pulled, it can drag the radially-poled permanent magnet 1602 with it. The radially-poled permanent magnet 1602 can be permanently or temporarily removed (FIG. 65B) (note removal path 1691) and the magnetic housing cap 1681 replaced (FIG. 65C). The actuator housing cap 1688 can then be replaced (FIG. 65D). The incision is then closed, and the subject may undergo typical MRI scanning. If desired, after the MRI scanning, the radially-poled permanent magnet 1602 may be replaced by following a reverse method. Alternatively, the magnetic housing cap 1681 or the actuator housing cap 1688 may be replaced by an alternatively shaped cap which will guide into a keyed structure within the magnet actuator 1604, thus keeping the internal mechanisms from turning, and keeping the subject's particular amount of adjustment from changing as the subject walks, runs or stretches.

Throughout the embodiments presented, a radially-poled permanent magnet (e.g. 168 of FIG. 8), as part of a magnetic assembly (e.g. 166), is used a driving element to remotely create movement in a non-invasively adjustable wedge osteotomy device. FIGS. 66-69 schematically show four alternate embodiments, wherein other types of energy transfer are used in place of permanent magnets.

Figure 66:
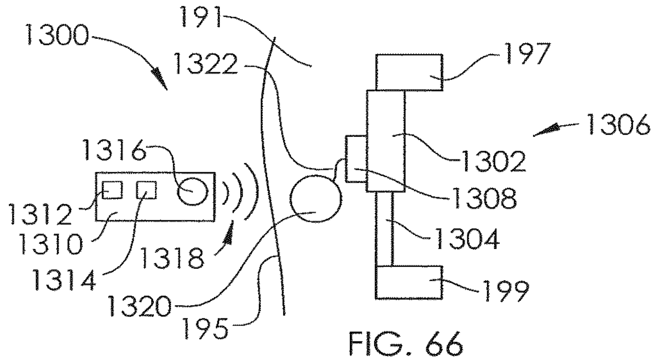
FIGS. 66-69 schematically illustrate various embodiments of alternate sources of a driving element of a non-invasively adjustable wedge osteotomy device.

FIG. 66 illustrates a non-invasively adjustable wedge osteotomy device 1300 comprising an implant 1306 having a first implant portion 1302 and a second implant portion 1304, the second implant portion 1304 non-invasively displaceable with relation to the first implant portion 1302. The first implant portion 1302 is secured to a first bone portion 197 and the second implant portion 1304 is secured to a second bone portion 199 within a patient 191. A motor 1308 is operable to cause the first implant portion 1302 and the second implant portion 1304 to displace relative to one another. An external adjustment device 1310 has a control panel 1312 for input by an operator, a display 1314 and a transmitter 1316. The transmitter 1316 sends a control signal 1318 through the skin 195 of the patient 191 to an implanted receiver 1320. Implanted receiver 1320 communicates with the motor 1308 via a conductor 1322. The motor 1308 may be powered by an implantable battery, or may be powered or charged by inductive coupling.

Figure 67:
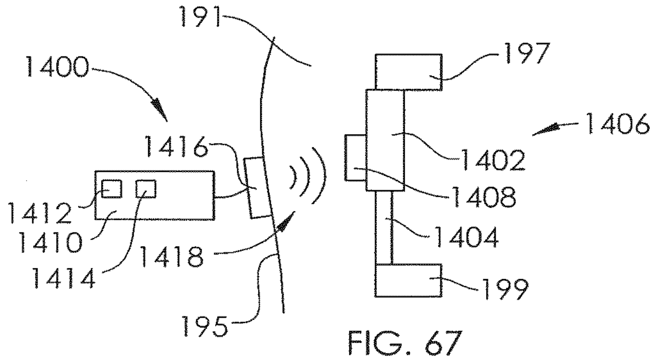

FIG. 67 illustrates a non-invasively adjustable wedge osteotomy device 1400 comprising an implant 1406 having a first implant portion 1402 and a second implant portion 1404, the second implant portion 1404 non-invasively displaceable with relation to the first implant portion 1402. The first implant portion 1402 is secured to a first bone portion 197 and the second implant portion 1404 is secured to a second bone portion 199 within a patient 191. An ultrasonic motor 1408 is operable to cause the first implant portion 1402 and the second implant portion 1404 to displace relative to one another. An external adjustment device 1410 has a control panel 1412 for input by an operator, a display 1414 and an ultrasonic transducer 1416, which is coupled to the skin 195 of the patient 191. The ultrasonic transducer 1416 produces ultrasonic waves 1418 which pass through the skin 195 of the patient 191 and operate the ultrasonic motor 1408.

Figure 68:
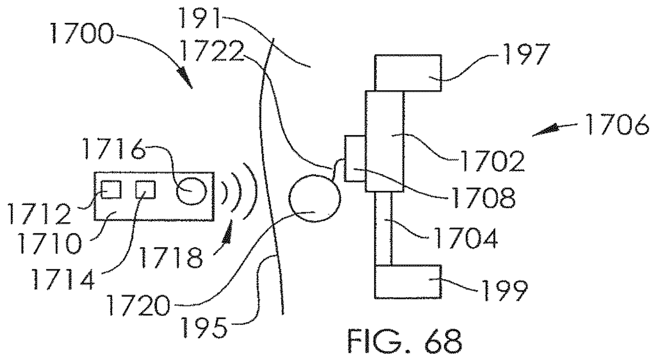

FIG. 68 illustrates a non-invasively adjustable wedge osteotomy device 1700 comprising an implant 1706 having a first implant portion 1702 and a second implant portion 1704, the second implant portion 1704 non-invasively displaceable with relation to the first implant portion 1702. The first implant portion 1702 is secured to a first bone portion 197 and the second implant portion 1704 is secured to a second bone portion 199 within a patient 191. A shape memory actuator 1708 is operable to cause the first implant portion 1702 and the second implant portion 1704 to displace relative to one another. An external adjustment device 1710 has a control panel 1712 for input by an operator, a display 1714 and a transmitter 1716. The transmitter 1716 sends a control signal 1718 through the skin 195 of the patient 191 to an implanted receiver 1720. Implanted receiver 1720 communicates with the shape memory actuator 1708 via a conductor 1722. The shape memory actuator 1708 may be powered by an implantable battery, or may be powered or charged by inductive coupling.

Figure 69:
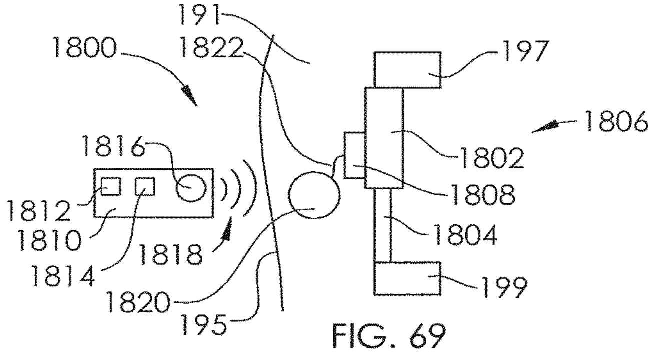

FIG. 69 illustrates a non-invasively adjustable wedge osteotomy device 1800 comprising an implant 1806 having a first implant portion 1802 and a second implant portion 1804, the second implant portion 1804 non-invasively displaceable with relation to the first implant portion 1802. The first implant portion 1802 is secured to a first bone portion 197 and the second implant portion 1804 is secured to a second bone portion 199 within a patient 191. A hydraulic pump 1808 is operable to cause the first implant portion 1802 and the second implant portion 1804 to displace relative to one another. An external adjustment device 1810 has a control panel 1812 for input by an operator, a display 1814 and a transmitter 1816. The transmitter 1816 sends a control signal 1818 through the skin 195 of the patient 191 to an implanted receiver 1820. Implanted receiver 1820 communicates with the hydraulic pump 1808 via a conductor 1822. The hydraulic pump 1808 may be powered by an implantable battery, or may be powered or charged by inductive coupling. The hydraulic pump 1808 may alternatively be replaced by a pneumatic pump.

In one embodiment a system for changing an angle of a bone of a subject includes an adjustable actuator having an outer housing and an inner shaft, telescopically disposed in the outer housing; a magnetic assembly configured to adjust the length of the adjustable actuator though axial movement of the inner shaft and outer housing in relation to one another; a first bracket configured for coupling to the outer housing; a second bracket configured for coupling to the inner shaft; and wherein application of a moving magnetic field externally to the subject moves the magnetic assembly such that the inner shaft and the outer housing move in relation to one another.

In another embodiment, a system for changing an angle of a bone of a subject includes a magnetic assembly comprising a radially-poled magnet coupled to a shaft having external threads; a block having internal threads and coupled to the shaft, wherein rotational movement of the radially-poled magnet causes the shaft to turn and to move axially in relation to the block; an upper bone interface and a lower bone interface having an adjustable distance; and wherein axial movement of the shaft in a first direction causes the distance to increase. The upper and lower bone interfaces may be formed as part of a plate spring. The upper and lower bone interfaces may be formed as part of a plurality of interlinked plates.

In another embodiment, a system for changing an angle of a bone of a subject includes a scissors assembly comprising first and second scissor arms pivotably coupled via a hinge, the first and second scissor arms coupled, respectively, to upper and lower bone interfaces configured to move relative to one another; a hollow magnetic assembly containing an axially moveable lead screw disposed therein, wherein the hollow magnetic assembly is configured to rotate in response to a moving magnetic field and wherein said rotation translations into axial movement of the lead screw; a ratchet assembly coupled at one end to the lead screw and at another end to one of the first and second scissor arms, the ratchet assembly comprising a pawl configured to engage teeth disposed in one of the upper and lower bone interfaces; and wherein axial movement of the lead screw advances the pawl along the teeth and moves the upper and lower bone interfaces away from one another In another embodiment, a method of preparing a tibia for implantation of an offset implant includes making a first incision in the skin of a patient at a location adjacent the tibial plateau of the tibia of the patient; creating a first cavity in the tibia by removing bone material along a first axis extending in a substantially longitudinal direction from a first point at the tibial plateau to a second point; placing an excavation device within the first cavity, the excavation device including a main elongate body and configured to excavate the tibia asymmetrically in relation to the first axis; creating a second cavity in the tibia with the excavation device, wherein the second cavity communicates with the first cavity and extends substantially towards one side of the tibia; and removing the excavation device. The second cavity may extend substantially laterally in the patient. The second cavity may extend substantially medially in the patient. The method may further include compacting a portion of the cancellous bone of the tibia in the creating a second cavity step. The excavation device may comprise an articulating arm having a first end and a second end, the arm including a compaction surface. The compaction surface may include a leading edge and at least one angled surface. The arm may be adjustable in relation to the main elongate body. The first end of the arm may be pivotally coupled to the main elongate body and the second end of the arm may be adjustable to a plurality of distances from the main elongate body. The excavation device may be coupled to an adjustment member configured to move the second end of the arm into at least one of the plurality of distances from the main elongate body. The creating a second cavity step may further comprise adjusting the adjustment member to move the second end of the arm along at least several of the plurality of distances from the main elongate body such that the compaction surface compacts cancellous bone against cortical bone. The creating a second cavity step may comprise removing bone material from the tibia. The excavation device may comprise an articulating arm having a first end and a second end, the arm including an abrading surface. The abrading surface may comprise a rasp. The arm may be adjustable in relation to the main elongate body. The first end of the arm may be pivotally coupled to the main elongate body and the second end of the arm may be adjustable to a plurality of distances from the main elongate body. The excavation device may be coupled to an adjustment member configured to move the second end of the arm into at least one of the plurality of distances from the main elongate body. The creating a second cavity step may further comprise moving the excavation device longitudinally along a bidirectional path approximating the first axis and adjusting the adjustment member to move the second end of the arm to at least one of the plurality of distances from the main elongate body such that the abrading surface removes bone material. The main elongate body may comprise a rotational cutting tool having a first end, a second end, a cutting region extending at least partially between the first end and second end, and a circumferential engagement member and the excavation device may further comprise a flexible drive train configured to engage the circumferential engagement member. The placing an excavation device step may further comprise creating a pathway through cortical bone on at least one side of the tibia, inserting the flexible drive train through a the pathway, and coupling the flexible drive train to the rotational cutting tool so that movement of the flexible drive train causes rotation of the rotational cutting tool. The creating a second cavity step may further comprise moving the circumferential engagement member of the rotational cutting tool substantially towards one side of the tibia while the rotational cutting tool is being rotated by the flexible drive train. The flexible drive train may be moved by drive unit. The rotational cutting tool may be used to create the first cavity. The rotational cutting tool may comprise a reamer. The first end of the rotational cutting tool may comprise a blunt tip. The second end of the rotational cutting tool may be coupled to a retrieval tether extending from the first incision. The retrieval tether may be coupled to the rotational cutting tool by a swivel joint. The removing step may comprise removing the rotational cutting tool by applying tension to the retrieval tether from a location external to the patient. The method may further comprise the step of creating an osteotomy between a first portion and a second portion of the tibia, wherein the flexible drive train extends through the osteotomy.

In another embodiment, a method of implanting a non-invasively adjustable system for changing an angle of the tibia of a patient includes creating an osteotomy between a first portion and a second portion of the tibia; making a first incision in the skin of the patient at a location adjacent the tibial plateau of the tibia of the patient; creating a first cavity in the tibia along a first axis extending in a substantially longitudinal direction from a first point at the tibial plateau to a second point; placing an excavation device within the first cavity, the excavation device configured to excavate the tibia asymmetrically in relation to the first axis; creating a second cavity in the tibia with the excavation device, wherein the second cavity extends substantially towards one side of the tibia; placing a non-invasively adjustable implant through the first cavity and at least partially into the second cavity, the non-invasively adjustable implant comprising an adjustable actuator having an outer housing and an inner shaft, telescopically disposed in the outer housing; coupling the outer housing to the first portion of the tibia; and coupling the inner shaft to the second portion of the tibia. The first portion may be above the osteotomy and the second portion may be below the osteotomy. The first portion may be below the osteotomy and the second portion may be above the osteotomy. The second cavity may communicate with the first cavity. The method may further comprise the step of non-invasively causing the inner shaft to move in relation to the outer housing. The non-invasively adjustable implant may comprise a driving element configured to move the inner shaft in relation to the outer housing. The driving element may be selected from the group comprising: a permanent magnet, an inductively coupled motor, an ultrasonically actuated motor, a subcutaneous hydraulic pump, a subcutaneous pneumatic pump, and a shape-memory driven actuator.

In another embodiment, a method of preparing a bone for implantation of an implant includes making a first incision in the skin of a patient; creating a first cavity in the bone by removing bone material along a first axis extending in a substantially longitudinal direction from a first point at the to a second point; placing an excavation device within the first cavity, the excavation device including a main elongate body and configured to excavate the bone asymmetrically in relation to the first axis, the excavation device further comprising an articulating arm having a first end and a second end, the arm including a compaction surface; creating a second cavity in the bone with the excavation device, wherein the second cavity communicates with the first cavity and extends substantially towards one side of the bone; and removing the excavation device.

In another embodiment, a method of preparing a bone for implantation of an implant includes making a first incision in the skin of a patient; creating a first cavity in the bone by removing bone material along a first axis extending in a substantially longitudinal direction from a first point at the to a second point; placing an excavation device within the first cavity, the excavation device including a main elongate body and configured to excavate the bone asymmetrically in relation to the first axis, the excavation device further comprising an articulating arm having a first end and a second end, the arm including an abrading surface; creating a second cavity in the bone with the excavation device, wherein the second cavity communicates with the first cavity and extends substantially towards one side of the bone; and removing the excavation device.

In another embodiment, a method of preparing a bone for implantation of an implant includes making a first incision in the skin of a patient; creating a first cavity in the bone by removing bone material along a first axis extending in a substantially longitudinal direction from a first point at the to a second point; placing an excavation device within the first cavity, the excavation device including a main elongate body and configured to excavate the bone asymmetrically in relation to the first axis, the excavation device further comprising a rotational cutting tool configured to be moved substantially towards one side of the bone while the rotational cutting tool is being rotated; creating a second cavity in the bone with the excavation device, wherein the second cavity communicates with the first cavity and extends substantially towards one side of the bone; and removing the excavation device.

In another embodiment, a system for changing an angle of a bone of a subject includes a non-invasively adjustable implant comprising an adjustable actuator having an outer housing and an inner shaft, telescopically disposed in the outer housing, the outer housing configured to couple to a first portion of the bone, and the inner shaft configured to couple to a second portion of the bone; a driving element configured to move the inner shaft in relation to the outer housing; and an excavation device including a main elongate body configured to insert within a first cavity of the bone along a first axis, the excavation device configured to excavate the bone asymmetrically in relation to the first axis to create a second cavity communicating with the first cavity, wherein the adjustable actuator is configured to be coupled to the bone at least partially within the second cavity. The driving element may be selected from the group comprising: a permanent magnet, an inductively coupled motor, an ultrasonically actuated motor, a subcutaneous hydraulic pump, a subcutaneous pneumatic pump, and a shape-memory driven actuator. The excavation device may be configured to compact cancellous bone. The excavation device may comprise an articulating arm having a first end and a second end, the arm including an abrading surface. The abrading surface may comprise a rasp. The excavation device may comprise a rotational cutting tool having a first end, a second end, a cutting region extending at least partially between the first end and second end, and a circumferential engagement member, and the excavation device may further comprise a flexible drive train configured to engage the circumferential engagement member.

In another embodiment, a system for changing an angle of a bone of a subject includes a non-invasively adjustable implant comprising an adjustable actuator having an outer housing and an inner shaft, telescopically disposed in the outer housing, the outer housing configured to couple to a first portion of the bone, and the inner shaft configured to couple to a second portion of the bone; and a driving element configured to move the inner shaft in relation to the outer housing, wherein the driving element is selected from the group comprising: a permanent magnet, an inductively coupled motor, an ultrasonically actuated motor, a subcutaneous hydraulic pump, a subcutaneous pneumatic pump, and a shape-memory driven actuator. The driving element may comprise a permanent magnet.

In another embodiment, a system for changing an angle of a tibia of a subject having osteoarthritis of the knee includes a non-invasively adjustable implant comprising an adjustable actuator having an outer housing and an inner shaft, telescopically disposed in the outer housing, the outer housing having a first transverse hole, and the inner shaft having a second transverse hole; a driving element configured to move the inner shaft in relation to the outer housing, wherein the driving element is selected from the group comprising: a permanent magnet, an inductively coupled motor, an ultrasonically actuated motor, a subcutaneous hydraulic pump, a subcutaneous pneumatic pump, and a shape-memory driven actuator; a first anchor configured to place through the first transverse hole and to couple to a first portion of the tibia; and a second anchor configured to place through the second transverse hole and to couple to a second portion of the tibia, wherein at least one of the first anchor and second anchor is configured to be pivotable in relation to the non-invasively adjustable implant when coupled to either the first portion or second portion of the tibia. The driving element may comprise a permanent magnet.

In another embodiment, a method of changing a bone angle includes creating an osteotomy between a first portion and a second portion of a tibia of a patient; creating a cavity in the tibia by removing bone material along an axis extending in a substantially longitudinal direction from a first point at the tibial plateau to a second point; placing a non-invasively adjustable implant into the cavity, the non-invasively adjustable implant comprising an adjustable actuator having an outer housing and an inner shaft, telescopically disposed in the outer housing, and a driving element configured to be remotely operable to telescopically displace the inner shaft in relation to the outer housing; coupling one of the outer housing or the inner shaft to the first portion of the tibia; coupling the other of the outer housing or the inner shaft to the second portion of the tibia; and remotely operating the driving element to telescopically displace the inner shaft in relation to the outer housing, thus changing an angle between the first portion and second portion of the tibia.

While embodiments of the present invention have been shown and described, various modifications may be made without departing from the scope of the present invention. Any of the embodiments of the non-invasively adjustable wedge osteotomy device may be used for gradual distraction (Ilizarov osteogenesis) or for acute correction of an incorrect angle. The implant itself may be used as any one of the elements of the excavation device, for example, the external portion of the implant may have features that allow it to be used as a reamer, rasp or bone compactor. As an alternative, remote adjustment described above may be replaced by manual control of any implanted part, for example manual pressure by the patient or caregiver on a button placed under the skin. The invention, therefore, should not be limited, except to the following claims, and their equivalents.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting a bone reamer into the first portion" include "instructing the inserting of a bone reamer into the first portion." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A system for changing an angle of a bone of a subject, the system comprising:

a non-invasively adjustable implant including an adjustable actuator having an outer housing and an inner shaft, telescopically coupled to the outer housing, the outer housing includes a threaded leadscrew, and the inner shaft includes a threaded nut interfacing with the threaded leadscrew, the outer housing includes a first bone anchor configured to couple to a first portion of the bone, and the inner shaft includes a second bone anchor configured to couple to a second portion of the bone;

a driver configured to rotate the threaded leadscrew relative to the threaded nut within the outer housing to move the inner shaft in axial relation to the outer housing; and an excavation device including:

a main elongate body configured to be inserted within a first cavity of the bone along a first axis, the main elongate body comprises a blunt distal tip, a distal reamer and a proximal reamer, the distal reamer includes a small diameter portion for insertion inside the proximal reamer;

a circumferential engagement member having several cutouts between the distal and proximal reamers and configured for engaging with external drive unit; and a flexible drive train configured to wrap around the circumferential engagement member the excavation device configured to rotate the excavation device about its longitudinal axis while applying lateral tension to pivot the excavation device about its blunt distal tip to excavate the bone asymmetrically in relation to the first axis to create a second cavity communicating with the first cavity, wherein the adjustable actuator is configured to be coupled to the bone at least partially within the second cavity.

2. The system of claim 1, wherein the driver is one of: a permanent magnet, an inductively coupled motor, an ultrasonically actuated motor, a subcutaneous hydraulic pump, a subcutaneous pneumatic pump, and a shape-memory driven actuator.

3. The system of claim 1, wherein the driver includes an inductively couplable motor configured to be non-invasively moved by a rotating external magnet inductively coupled to the driver.

4. The system of claim 1, wherein the excavation device is configured to compact cancellous bone.

5. A system for changing an angle of a tibia of a subject, the system comprising:

a non-invasively adjustable implant including an adjustable actuator having an outer housing and an inner shaft, telescopically disposed in the outer housing, the outer housing includes a threaded leadscrew, and the inner shaft includes a threaded nut interfacing with the threaded leadscrew, the outer housing includes a first bone anchor configured to couple to a first portion of the bone, and the inner shaft includes a second bone anchor configured to couple to a second portion of the bone which is separated from the first bone by a wedge that has been cut from the tibia; and a driver configured to rotate the threaded leadscrew relative to the threaded nut within the outer housing to move the inner shaft in axial relation to the outer housing, wherein the driver includes one of: a permanent magnet, an inductively coupled motor, an ultrasonically actuated motor, a subcutaneous hydraulic pump, a subcutaneous pneumatic pump, and a shape-memory driven actuator;

an excavation device including:

a main elongate body configured to be inserted within a first cavity of the bone along a first axis, the main elongate body comprises a blunt distal tip, a distal reamer and a proximal reamer, the distal reamer includes a small diameter portion for insertion inside the proximal reamer;

a circumferential engagement member having several cutouts between the distal and proximal reamers and configured for engaging with external drive unit; and a flexible drive train configured to wrap around the circumferential engagement member the excavation device configured to rotate the excavation device about its longitudinal axis while applying lateral tension to pivot the excavation device about its blunt distal tip to excavate the bone asymmetrically in relation to the first axis to create a second cavity communicating with the first cavity, wherein the adjustable actuator is configured to be coupled to the bone at least partially within the second cavity.

6. The system of claim 5, wherein the driver comprises a permanent magnet.

7. The system of claim 5, wherein the driver includes an inductively couplable motor configured to be non-invasively moved by a rotating external magnet inductively coupled to the driver.

8. The system of claim 5, wherein the excavation device is configured to compact cancellous bone.

* * * * *